(12) United States Patent
Behlow, Jr. et al.

(10) Patent No.: US 8,384,372 B1
(45) Date of Patent: Feb. 26, 2013

(54) NON-LINEAR ELECTRICAL ACTUATION AND DETECTION

(75) Inventors: Herbert W. Behlow, Jr., Greenville, SC (US); Bevan C. Elliott, Greenville, SC (US); Gayatri D. Keskar, Stamford, CT (US); Doyl E. Dickel, Central, SC (US); Malcolm J. Skove, Clemson, SC (US); Apparao M. Rao, Anderson, SC (US)

(73) Assignee: Clemson University, Clemson, SC (US)

( * ) Notice: Subject to any disclaimer, the term of this patent is extended or adjusted under 35 U.S.C. 154(b) by 377 days.

(21) Appl. No.: 12/573,433

(22) Filed: Oct. 5, 2009

Related U.S. Application Data

(63) Continuation-in-part of application No. 11/354,268, filed on Feb. 14, 2006, now Pat. No. 7,598,723.

(60) Provisional application No. 60/652,754, filed on Feb. 14, 2005, provisional application No. 60/708,149, filed on Aug. 15, 2005.

(51) Int. Cl.
*G01R 13/34* (2006.01)
(52) U.S. Cl. .................. 324/76.42; 324/76.41
(58) Field of Classification Search ............ 324/76.42
See application file for complete search history.

(56) References Cited

U.S. PATENT DOCUMENTS

| | | | |
|---|---|---|---|
| 4,805,456 A | 2/1989 | Howe et al. | |
| 5,258,923 A | 11/1993 | Imam et al. | |
| 5,266,896 A | 11/1993 | Rugar et al. | |
| 5,306,412 A | 4/1994 | Whitehouse et al. | |
| 5,442,288 A | 8/1995 | Fenn et al. | |
| 5,559,358 A * | 9/1996 | Burns et al. | 257/431 |
| 5,719,324 A | 2/1998 | Thundat et al. | |
| 5,807,758 A * | 9/1998 | Lee et al. | 436/526 |
| RE36,603 E | 3/2000 | Pohl et al. | |
| 6,249,000 B1 | 6/2001 | Muramatsu et al. | |
| 6,311,549 B1 | 11/2001 | Thundat et al. | |
| 6,368,275 B1 | 4/2002 | Sliwa et al. | |
| 6,444,927 B1 | 9/2002 | Korpi | |
| 6,555,945 B1 | 4/2003 | Baughman et al. | |
| 6,593,731 B1 | 7/2003 | Roukes et al. | |
| 6,642,129 B2 | 11/2003 | Liu et al. | |
| 6,668,627 B2 | 12/2003 | Lange et al. | |
| 6,676,813 B1 | 1/2004 | Pelekhov et al. | |
| 6,722,200 B2 | 4/2004 | Roukes et al. | |
| 6,734,425 B2 | 5/2004 | Hantschel et al. | |
| 6,823,724 B1 | 11/2004 | Kobayashi et al. | |

(Continued)

OTHER PUBLICATIONS

San Paulo, A. et al., Mechanical elasticity of single and double clamped silicon nanobeams fabricated by the vapor-liquid-solid method, App. Phys. Ltrs., 87, 053111, 2005, p. 053111-1 to p. 053111-3.*

(Continued)

*Primary Examiner* — Thomas Valone
(74) *Attorney, Agent, or Firm* — Dority & Manning, P.A.

(57) ABSTRACT

A method and system is disclosed to detect and analyze an electric signal based on movement between an element and a counter electrode influenced by a nonlinear electric field produced by an electrical signal impressed between the element and counter electrode. Through detection of changes in the distance between the element and the counter electrode characteristics of the element and/or the environment of the element may be ascertained. Changes in the distance between the element and the counter electrode may be monitored based on changes in the value of capacitance between the element and counter electrode. The disclosed devices and methods may be employed to detect, for instance, presence of chemical/biological species in a sample or measure physical parameters of a sample such as pressure/acceleration, density, viscosity, magnetic force, temperature, and/or extremely small masses.

20 Claims, 15 Drawing Sheets

U.S. PATENT DOCUMENTS

| | | | |
|---|---|---|---|
| 6,845,655 | B2 | 1/2005 | van der Weide et al. |
| 6,879,012 | B2 | 4/2005 | Tang et al. |
| 6,894,272 | B2 | 5/2005 | Kranz et al. |
| 6,910,382 | B2 | 6/2005 | Tang et al. |
| 6,935,167 | B1 | 8/2005 | Sahin et al. |
| 7,068,027 | B1 | 6/2006 | Mastro et al. |
| 2006/0075836 | A1* | 4/2006 | Zribi et al. ............. 73/866.1 |
| 2006/0150719 | A1 | 7/2006 | Reinstadtler et al. |

OTHER PUBLICATIONS

Minne, S.C. et al., Parallel atomic force microscopy using cantilevers with integrated piezoresistive sensors and integrated piezoelectric actuators, Appl. Phys. Lett. 67, 1995, p. 3918-3921.*

Fontaine, P. et al., A critical look at surface force measurement using a commercial atomic force microscope in the noncontact mode, Rev. Sci. Inst., 68, 11, Nov. 1997, p. 4145-4151.*

Rousier, R. Measurement of the contact potential difference with an electrostatic force microscope, Eur. J. Phys., 22, 2001, 657-662.*

Pinnaduwage, L.A. et al., Sensitive detection of plastic explosives with self-assembled monolayer-coated microcantilevers, App. Phys. Lett., V. 83, No. 7, 2003, p. 1471-1473.*

Wang, Z.L., New developments in transmission electron microscopy for nanotechnology, Adv. Mater. 2003, 15, No. 18, Sep. 16, p. 1497-1513.*

Abstract of Article—*Electrical Detection of Oscillations in Micro- and Nano- Cantilevers Using Harmonic Detection of Resonance*, Gaillard et al., Materials Research Society, Symposium Proceedings, 2006, vol. 888, 1 page.

Article—*A New Tunneling-Based Sensor for Inertial Rotation Rate Measurements*, Kubena et al., Journal of Microelectromechanical Systems, vol. 8, No. 4, Dec. 1999, pp. 439-447.

Article—*Active Sensing in Ambient Conditions Using an Electrostatically Driven Silicon Microcantilever*, Keskar et al., Sensors & Transducers Journal, vol. 91, Issue 4, Apr. 2008, pp. 1-13.

Article—*An analytic characterization of the harmonic detection of resonance method*, Dickel et al., Journal of Applied Physics, vol. 106, 2009, pp. 044515-1-044515-6.

Article—*Determination of the Bending Modulus of an Individual Multiwall Carbon Nanotube using an Electric Harmonic Detection of Resonance Technique*, Ciocan et al., Nano Letters, vol. 5, No. 12, 2005, pp. 2389-2393.

Article—*Electrical detection of oscillations in microcantilevers and nanocantilevers*, Gaillard et al., Review of Scientific Instruments, vol. 77, 2006, 073907-1-073907-5.

Article—*Mechanical properties of chemical vapor deposition-grown multiwalled carbon nanotubes*, Gaillard et al., Applied Physics Letters, vol. 86, 2005, pp. 233109-1-233109-3 2.

Article—*Ultra-Sensitive Duffing Behavior of a Microcantilever*, Keskar et al., IEEE Sensors Journal, vol. 8, No. 11, Nov. 2008, pp. 1848-1855.

Article—*Using electric actuation and detection of oscillations in microcantilevers for pressure measurements*, Keskar et al., Sensors and Actuators A: Physical, vol. 147, 2008, pp. 203-209.

Paper from Technology Review—The Impact of Emerging Technologies: Demo: Sensing Success by David Rotman, Dec. 2005/Jan. 2006, 14 pages, www.technologyreview.com.

Poster from Clemson University entitled *Determination of Nanotube Density by Gradient Sedimentation* by Lu et al., prepared for the Sixth International Conference on the Science and Application of Nanotubes, 2005, Gothenburg, Sweden, Jun. 2005, 1 page.

* cited by examiner

NON-LINEAR ELECTRICAL ACTUATION AND DETECTION

CROSS REFERENCE TO RELATED APPLICATIONS

This application claims priority as a Continuation-In-Part Application of previously filed U.S. patent application Ser. No. 11/354,268, filed Feb. 14, 2006, and claims benefit of Provisional Application Ser. No. 60/652,754, filed on Feb. 14, 2005 and Provisional Application Ser. No. 60/708,149 filed on Aug. 15, 2005.

FEDERALLY SPONSORED RESEARCH AND DEVELOPMENT

The United States Government may have rights in this invention pursuant to National Science Foundation Grant No. 2003863.

BACKGROUND OF THE INVENTION

The ability to build extremely small devices via recently discovered micro- and nano-fabrication processes has opened the door to the possibility of electromechanical machines and sensors of a size existing only in the realm of science fiction in previous generations. For instance, many methods now exist to build working microelectromechanical systems (MEMS) as well as even smaller nanoelectromechanical systems (NEMS). While the technology to build these devices is continuing to expand and grow, practical applications for such devices remain elusive. Problems currently faced by researchers in taking this final step often center around the challenges to be overcome in regard to communicating to the macroscopic world the mechanical motion and/or the electronic signals generated on the micro- or nano-sized scale. For instance, as the devices are so small, the capacitance of a signal junction can approach the unavoidable parasitic capacitance due to the existence of junctions between components of the device, as well as the resting capacitance of the device itself. As such, the devices can describe an extremely low signal to noise ratio, making the detection of an electrical signal very difficult, if not impossible.

Some of the primary mechanical elements being utilized in the development of MEMS and NEMS technology include micro- and nano-sized cantilevers, clamped beams, and the like. Such devices are often used in sensing or actuating technologies and are generally based upon the changes in a property of the cantilever or beam due to absorption or adsorption of a species at the surface or due to changes in the physical characteristics of a sample including, for instance, pressure/acceleration changes, magnetic force changes, temperature changes, and/or extremely small changes in mass. Detection of change in resonant frequency of a device is one particular mechanical property that has been used in many such regimes. Changes in the oscillating or resonant frequency of a micro- or nano-sized beam have generally been limited to determination through optical detection, e.g., analysis of the deflection properties of a laser directed at a reflecting surface of the cantilever, analysis and detection of changes in the resistivity of a piezoresistor integrated into the cantilever, or analysis of magnetically induced signals.

Difficulties exist with these detection methods, however. For instance, optical detection techniques require optical access to the cantilever as well as the utilization of relatively expensive laser technologies. Integration of a piezoresistor to a cantilever so as to detect changes in resistivity on the material can necessitate increase in size as well as cost of the apparatus. Also, the large magnetic fields required in magnetic systems can be difficult and expensive to establish. Accordingly, there remains room for variation and improvement within the art.

SUMMARY OF THE INVENTION

In general, the present invention is directed to methods for detecting resonance in semi-conductive or conductive elements and devices that utilize the disclosed method. For instance, the method can include applying a signal to a counter electrode and thereby inducing an electrostatic force on an element that is in a non-contact arrangement with one or more counter electrodes. In response to the electrostatic force, an electric signal can be generated at the element. At resonance, this signal will contain not only the fundamental mode of the applied signal, but will also contain harmonics of the applied signal. Hence, the disclosed methods include examining this generated signal to ascertain the presence of one or more of the harmonics of the applied signal in order to detect resonance in the element. For example, the generated signal can be examined to ascertain the presence of the second harmonic or the third harmonic of the applied signal or selected sub-harmonics of the applied signal.

In one particular embodiment, the frequency of the generated signal can be examined to determine the presence of higher harmonics of the applied signal. For instance, both the applied and generated signals can be fed to a signal processor such as a lock-in amplifier, and the frequencies of the signals can be examined for the presence of higher harmonics in the generated signal. If desired, the process can also include determination of the Quality factor of the generated signal.

The elements of the disclosed devices and the counter electrode(s) can be micro- or nano-sized elements and may be fabricated using CMOS technology on an integrated chip or may be separate pieces with differing structures. In general, the elements can be less than about 500 μm in length and less than about 50 μm in width. In one embodiment, the elements can be nano-sized. For example, the element can be less than about 500 nm in width, for example a single walled nanotube of about 1 nm in diameter. In one embodiment, the element can include one or more carbon-based nanostructures. For instance, the element can include a carbon nanotube. In additional embodiments the element may be a silicon microcantilever, a silicon microcantilever coated with a metal such as gold, platinum, etc., a nano-scale silicon or coated silicon nano-cantilever, a metallic or conducting nano-wire or nano-ribbon. The elements can also have any suitable geometry and orientation in the device. For example, the element can be a single-clamped cantilever or a double-clamped beam. In certain embodiments the counter electrode may be a chemically etched tungsten wire, a metallic wire of any kind, or any conducting wire, plate, or other shape, such as a sphere.

The spatial relationship between the counter electrode and the element may be configured such that an electrostatic force can be induced on the element. For instance, the element and the counter electrode can be in a parallel arrangement or a tip-to-tip arrangement. Beneficially, the two can be farther apart than thought possible in MEMS and NEMS systems of the past, due to the resonant detection regime described herein. For instance, a micro-sized system can have the two in parallel arrangement and between about 10 μm and about 20 μm apart, in one embodiment. In alternate embodiments of the present subject matter, the elements may be spaced 1-5 microns apart. And when considering a nano-sized element, one embodiment of the invention includes the element and the counter electrode located between about 10 nm and about 2 µm apart from one another.

The disclosed devices can include any device in which the direct electric detection of resonance in an element can be beneficial. For instance, in certain embodiments the disclosed devices can include chemical sensors in which the resonant frequency of the element can change upon the interaction of the element with a chemical species. Accordingly, the element of the device can be monitored for a change in resonant frequency, for instance through application of a modulated signal to the counter electrode, and a detected change in resonant frequency can signal the presence of a species of interest. While the interaction of the element and the species can include contact, for instance adsorption of the species onto the element, this is not a requirement of the invention, and in other embodiments, the interaction need not include actual contact.

Other electrical devices encompassed by the present invention include, but are not limited to, atomic force microscopes (AFM), high Q-factor oscillators, switching devices, and antennas.

BRIEF DESCRIPTION OF THE FIGURES

A full and enabling disclosure of the present invention, including the best mode thereof, to one of ordinary skill in the art, is set forth more particularly in the remainder of the specification, including reference to the accompanying figures in which.

Figure 1:
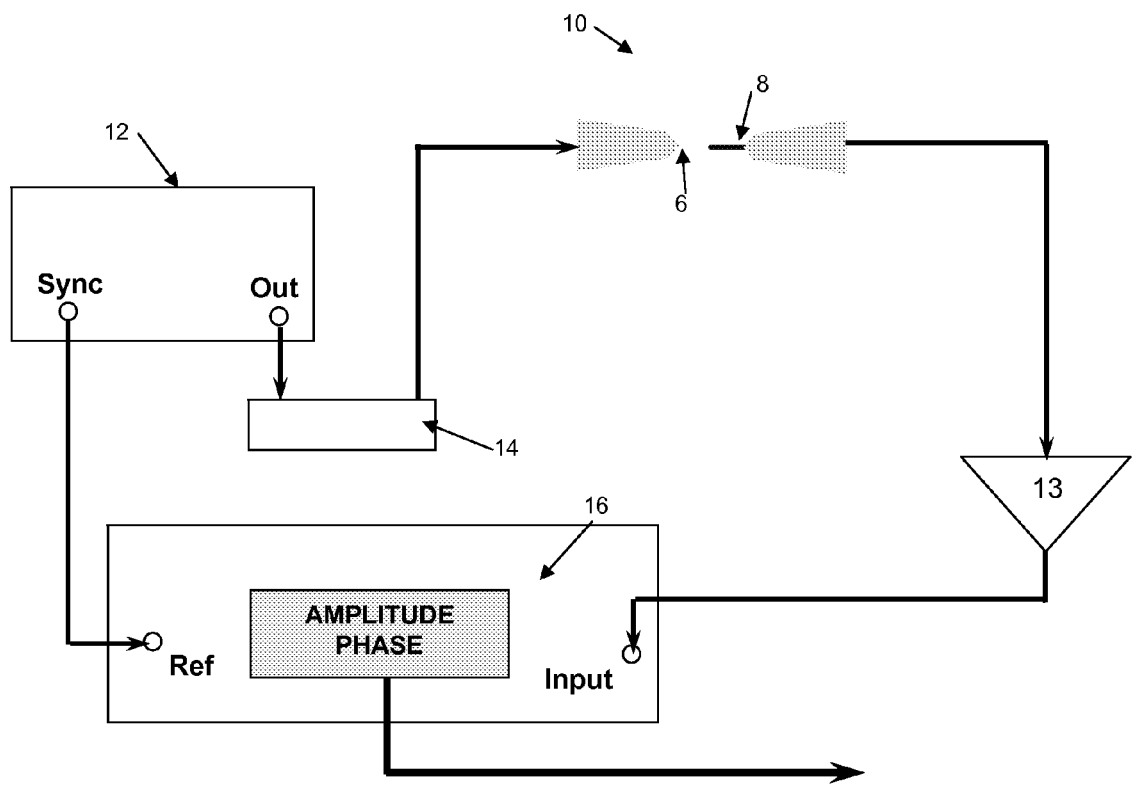
FIG. 1 is a schematic diagram of one embodiment of a system of present invention.

Repeat use of reference characters in the present specification and drawings is intended to represent the same or analogous features or elements of the present invention.

DETAILED DESCRIPTION OF PREFERRED EMBODIMENTS

Reference will now be made in detail to various embodiments of the invention, one or more examples of which are illustrated in the accompanying Figures. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used with another embodiment to yield a still further embodiment. Thus, it is intended that the present invention cover such modifications and variations as come within the scope of the appended claims and their equivalents.

In general, the present invention is directed to micro- and nano-sized electromechanical systems including micro- or nano-sized elements that can be electrostatically driven to resonance. More specifically, utilizing the disclosed devices and methods, direct electronic detection of the resonant frequency, changes of the resonant frequency, and associated phase signal of a micro- or nano-sized element such as a cantilever or double-clamped beam is possible. According to one embodiment of the present subject matter, resonance of an element can be directly detected through analyses of the electronic signal induced in the element at resonant vibration. For instance, one or both of the amplitude and phase of an electronic signal generated in the element at resonance can be directly detected and analyzed. Beneficially, changes in the resonant frequency of an element can be directly determined at ambient temperatures and pressures according to one embodiment of the disclosed invention. In accordance with further embodiments of the present subject matter, analysis of an acquired waveform may be employed to determine amplitude and phase relationship with respect to a driving signal or to one another of each of plural harmonics to provide additional data.

The presently disclosed processes and systems can facilitate the formation of economical, portable NEMS and MEMS devices suitable for use in practical, real-world applications. The disclosed methods can be utilized with other devices as well, for instance, the disclosed methods can be utilized in development of high quality electronic filters as well as other high quality (high Q factor) electronic devices.

Devices constructed in accordance with the present subject matter can include one or more micro-sized or nano-sized elements. For example, the devices can utilize one or more micro-sized beams as have been utilized as micro-sized cantilevers in previously known devices that utilize optical or piezoresistor resonance detection schemes. In general, micro-sized beams can be classified as those having micrometer dimensions, e.g., greater than about 1 µm in width and/or thickness. For example, micro-cantilevers of the present invention can have a length dimension less than about 500 µm, for instance between about 90 µm and about 350 µm and a width dimension less than about 50 µm, for instance between about 10 µm and about 50 µm, for instance about 35 µm wide. Nano-sized elements of the present invention generally include those elements having width and/or thickness dimensions less than the micro-sized devices (e.g., less than about 1 µm). For instance, in one embodiment, nano-sized elements of the invention can have a width and/or thickness dimension less than about 500 nm. Nano-sized elements can, however, have a length in the micrometer range. For instance, one exemplary nano-cantilever of the invention can have a generally circular cross-section of between about 1 nm and about 200 nm in diameter, and a length in the micrometer range, for instance greater than about 5 µm.

In general, the elements of the devices can have any geometric shape and can have an aspect ratio (L/D) greater than about two. As such, throughout much of the following discussion, the elements of the present invention are synonymously referred to as beams. Moreover, though much of the following discussion is directed to embodiments in which the elements or beams of the invention are provided in a device as a cantilever, i.e., clamped at a first end and free to vibrate at a second end, the presently disclosed methods and devices are equally applicable to an element provided in other orientations. For example, the invention is also directed to devices in which the disclosed element is clamped at both ends, i.e., a double-clamped beam. In particular, the presently disclosed invention encompasses any micro- or nano-sized element that can be electrostatically driven into resonance.

The elements of the disclosed devices can generally be formed of any material including a suitable conductive or semi-conductive material at least at the surface of the element. For instance, in one embodiment, an element can be formed of a non-conductive base substrate that has been coated with a conductive outer layer. Fabrication materials and techniques for forming many structures suitable for use in the presently disclosed devices are generally known to those of ordinary skill in the art. For example, materials encompassed by the invention include metallic nanowires, gallium arsenide/aluminum arsenide structures, nanocrystalline diamond films, and materials based upon silicon including, but not limited to, silicon on insulator structures, silicon carbide on silicon structures, aluminum nitride on silicon structures, and amorphous silicon nitride structures. In other embodiments, the element may be a silicon microcantilever, a silicon microcantilever coated with a metal such as gold, platinum, etc., a nano-scale silicon or coated silicon nano-cantilever, a metallic or conducting nano-wire or nano-ribbon.

In one embodiment, the elements of the disclosed devices can be nanostructures, and in one particular embodiment, carbon-based nanostructures. For example, carbon-based nano-cantilevers of the disclosed devices can be formed from nanotubes, including single-walled nanotubes (SWNT) and multi-walled nanotubes (MWNT), nanobelts, nanorods, nanowires, nanocoils, and the like. In addition, the elements can be formed of more than one nanostructure in combination, for example, a bundle of nanotubes, or a stack of nanobelts, or even combinations of two or more structures of different shapes. Nanostructures of the invention are not limited to carbon-based nanostructures, however, and nanostructures formed of other material can be utilized. For example, nanostructures etched from silicon or including any other suitable conductive or semi-conductive material at the surface can be utilized.

Carbon nanostructures are known to exhibit exceptional physical strength, elasticity, adsorption capability, and high specific surface area. In addition, mechanical characteristics of individual carbon nanostructures have been found to be sensitive to physical characteristics of the structures that can be affected via formation materials and methods. For example, the bending modulus of individual nanostructures has been found to be sensitive to the density of wall defects formed in the structure. As such, the elements of the present invention can, in one embodiment, be specifically designed with particular, predetermined mechanical characteristics, such as a particular bending modulus, for instance, for utilization in a particular environment or for detection of a particular species or analyte.

In certain embodiments of the present subject matter the ability of carbon nanostructures to quickly adsorb materials is of benefit to the disclosed devices in certain sensing applications. For instance, upon adsorption of a sample material onto an element, e.g., a carbon-based nano-cantilever, the inherent physical properties of the element can be affected. In particular, the elastic properties and the natural resonant frequency of the element can vary depending upon exactly what substances have been adsorbed. Thus, a shift in resonant frequency can be observed upon adsorption of a substance. Moreover, this shift can vary depending on what material has been adsorbed. Beneficially, as many materials that can form the disclosed elements are naturally highly adsorbent, certain embodiments of the present invention may not require pre-functionalization of the element, and as such, the formation processes for such embodiments can be relatively simple and inexpensive. In other embodiments of the present subject matter, absorption of materials is neither required nor desired so that other appropriate materials may be selected for the element.

In general, the elements of the disclosed devices can be formed according to any known formation method and of any suitable material. For example, carbon-based nano-cantilevers of the invention can be formed via physical evaporation methods such as vapor-liquid-solid (VLS) processes, chemical vapor deposition (CVD) methods, catalyst assisted processes, processes involving electric arc gas discharge, or pulsed laser ablation techniques, as are generally known to those of ordinary skill in the art.

In addition, the physical characteristics such as the bending modulus of the beams can be altered through selection of particular formation methods, functionalization of the base materials, and/or addition of dopants to the materials. As such, elements of the invention can be engineered so as to exhibit particular physical characteristics for use, for example, in a particular environment or for detection of one or more particular analytes from a sample.

In certain embodiments of the present invention, the disclosed devices can be made more sensitive by degassing the material forming the element. In this particular embodiment, the devices can respond to the presence of species, such as in a gaseous or vaporous sample, in concentration levels as little as about 100 ppb.

In addition, when the material is degassed prior to use, the devices can have measurable response to an increased number of materials. For example, when utilizing degassed carbon-based nanostructures, systems of the invention can indicate a measurable variation in resonant frequency upon exposure to polar as well as non-polar materials.

Figure 9:
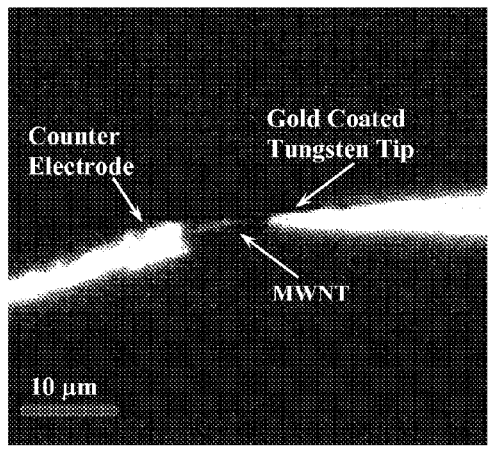
FIG. 9 is a dark field image of a tip to tip configuration of a nano-cantilever according to one embodiment of the present invention.
Figure 16:
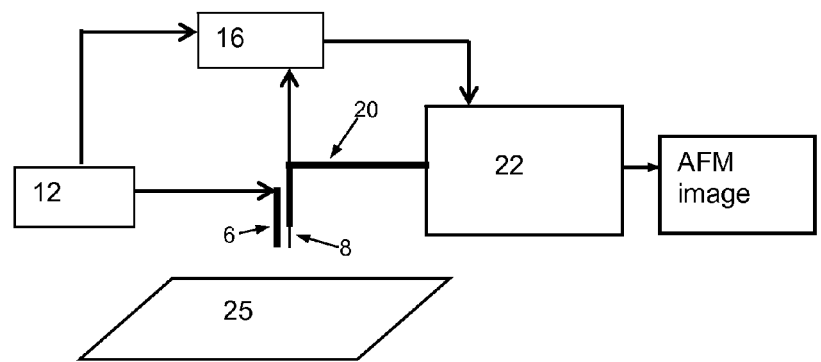
FIG. 16 is a schematic illustration of one embodiment of an AFM system utilizing methods and devices of the present invention.

One embodiment of a cantilever-based device of the present invention is schematically illustrated in FIG. 1. As can be seen in the Figure, the system can include a cantilever assembly 10 that can include a micro- or nano-sized cantilever 8 in proximity to a counter electrode 6 in a tip-to-tip arrangement. FIG. 9 is a dark field image of one such embodiment of a cantilever assembly in which the cantilever 8 and the counter electrode 6 are in tip-to-tip association with one another. The cantilever in this particular embodiment is a single MWNT. FIGS. 3A, 3B, and 16 illustrate another possible arrangement of the cantilever assembly 10 of the present systems in which the cantilever 8 and the counter electrode 6 are in a parallel arrangement.

Referring again to FIG. 1, the system can also include a signal generator 12 to generate an ac voltage that can be applied to the counter electrode 6 at varying frequencies. In general, a dc offset can also be supplied, as at 14, and also applied to the counter electrode 6. The dc offset can balance the difference between surface work functions of the counter electrode and the cantilever, respectively. The dc offset can also be utilized to modify the amplitude and frequency of the resonance, providing the capability of tuning the circuit, which can be useful in a number of electronic devices and applications.

The counter electrode 6 can be in close enough proximity to the element, e.g., the cantilever 8, so as to induce a charge on the element while remaining in a non-contact mode. The preferred gap distance between the counter electrode 6 and the cantilever 8 can vary, and can depend, for instance, upon the nature of the atmosphere surrounding the system and on the geometric relationship between the cantilever and the counter electrode. In general, however, the intervening distance between the cantilever 8 and the counter electrode 6 can be at least enough so as to ensure no contact between the counter electrode and the cantilever at resonance, while ensuring the capability of establishing a capacitance driven electrostatic force on the cantilever.

The voltage applied to the counter electrode acts as a drive signal and induces an electrostatic force on the cantilever, which, at the appropriate parameters, can force the cantilever to vibrate at its mechanical resonance. A circuit for electrically driving and detecting the motion of the cantilever can include a signal generator, a DC voltage source, a signal amplifier, and an instrument such as an oscilloscope for measuring the electrical output of the circuit. In one particular embodiment, a modulated voltage driving signal can be applied, so as to induce a modulated electrostatic force on the cantilever. The modulated driving signal may correspond to a sine wave, square wave, sawtooth, or triangular wave, or a sum of sine waves at different frequencies, or a complex waveform consisting of a combination of any of the above. Further the drive signal may be applied continuously or in an on/off manner. In the tip to tip configuration, a tunneling gap could be created between the cantilever and the counter electrode and the tunneling current used as the drive signal.

According to the first embodiment of the present subject matter, unique characteristics of a system at resonance have been recognized and utilized to provide a method for direct electronic detection of a signal generated by a micro- or nano-sized element at resonance. More specifically, the presently disclosed methods and systems recognize and utilize the fact that at resonance, the force between the counter electrode 6 and the cantilever 8, and thus the charge induced in the cantilever, not only includes a term that oscillates at the fundamental, i.e., resonant frequency, $\omega_o$, but also includes terms that oscillate at harmonics of the resonant frequency, e.g., $2\omega_o$, $3\omega_o$, etc., as well as sub-harmonics thereof. In accordance with further embodiments of the present subject matter, it has also been found that the phase relationships and amplitudes among the various harmonics and the driving signal also varies depending on the cantilever's environmental conditions. This aspect of the present subject matter will be discussed more fully later.

While not wishing to be bound by any particular theory, it is believed that when a voltage $V(t)=V_{dc}+W+V_{oc}\cos(\omega t)$ is placed on the counter electrode (where $V_{ac}\cos(\omega t)$ and $V_{dc}$ are the applied ac and dc voltages, and W is the difference between the work potentials of the cantilever and counter electrode) and when $\omega$ approaches $\omega_0$ (the resonant frequency of the cantilever) the harmonic terms of the resonating cantilever can be detected. According to the theory, let $C(t)$ be the capacitance between the cantilever and the counter electrode. The electrostatic energy of the system is then $\frac{1}{2}CV^2$, and the force on the cantilever is $$F = \frac{-1}{2}\frac{dCV^2}{dx} = \frac{-1}{2}V^2\frac{dC}{dx}.$$

If the vibration amplitude $x(t)$ of the cantilever is small compared to the distance $x_0$ between the cantilever and the counter electrode, then $$C(t) \approx C_0 + \frac{dC}{dx}\bigg|_{x=0}x(t), \text{ where } C_0 \text{ and } \frac{dC}{dx}\bigg|_{x=0} = -C'_0$$

are constants for a given experimental set up. Thus for small deflections, the Coulomb force on the cantilever is $$F_c = 1/2C'_0(V_{dc} + W + V_{ac}\cos(\omega t))^2 = 1/2C'_0 \qquad \text{S(1)}$$
$$\left\{(V_{dc}+W)^2 + 2(V_{dc}+W)V_{ac}\cos(\omega t) + \frac{1}{2}V_{ac}^2[1+\cos(2\omega t)]\right\}$$

(Note that $C_0'$ is a function of the geometry of the system.) If the vibration amplitude is not small compared with the separation of the counter electrode and the cantilever, or if the geometry of the capacitance is complex, terms of higher order in $x(t)$ needs to be considered as it is these higher order terms (mechanical harmonics) that are of significance to the present subject matter, as will be more fully discussed later. When $\omega$ is close to a normal mode frequency $\omega_0$ of the free cantilever, and the damping is small, the steady state solution for $x(t)$ is $$x(t) = \frac{QC_0'(V_{dc}+W)V_{ac}\cos(\omega t - \phi_1)}{k'\sqrt{Q^2\left[1-\left(\frac{\omega}{\omega_0'}\right)^2\right]^2 + \frac{\omega^2\omega_0^2}{\omega_0'^4}}}, \quad \tan\phi_1 = \frac{\omega_0\omega}{Q(\omega_0'^2-\omega^2)} \quad \text{S(2)}$$

where $\omega_o'^2 = k'/m$, $k' = k - dF_e/dx$, m is the inertial term of the vibrational mode, and Q the quality factor of the mode in the environment of the experiment. The electrostatic correction term $dF_e/dx$ is usually small, as discussed below, so that $\omega_o'$ is not very different from $\omega_o$. Since F also has a term that oscillates at $2\omega$, when $2\omega$ is close to $\omega_o$ a similar analysis gives:

$$x(t) = \frac{QC_0'V_{ac}^2\cos(2\omega t - \phi_2)}{4k'\sqrt{Q^2\left[1-\left(\frac{2\omega}{\omega_0'}\right)^2\right]^2 + \frac{4\omega^2\omega_0^2}{\omega_0'^4}}}, \quad \text{S(3)}$$

$$\tan\phi_2 = \frac{2\omega_0\omega}{Q(\omega_0'^2 - 4\omega^2)}$$

Since $q(t) = C(t)V(t)$, to first order in $x(t)$, we obtain for the time dependent part of q:

$$q(t) = \left[C_0 - \frac{QC_0'^2(V_{dc}+W)V_{ac}\cos(\omega t - \phi_1)}{k'\sqrt{Q^2\left[1-\left(\frac{\omega}{\omega_0'}\right)^2\right]^2 + \frac{\omega^2\omega_0^2}{\omega_0'^4}}}\right][V_{ac}\cos(\omega t)] \quad \text{(S4)}$$

$\omega$ near $\omega_0$ $$= [C_0 V_{ac}\cos(\omega t)] - \left[\frac{QC_0'^2(V_{dc}+W)V_{ac}}{2k'\sqrt{Q^2\left[1-\left(\frac{\omega}{\omega_0'}\right)^2\right]^2 + \frac{\omega^2\omega_0^2}{\omega_0'^4}}}\right]$$

$$[\cos(2\omega t + \phi_1) + \cos\phi_1]$$

and $$q(t) = \left[C_0 - \frac{QC_0'V_{ac}^2\cos(2\omega t - \phi_2)}{4k'\sqrt{Q^2\left[1-\left(\frac{2\omega}{\omega_0'}\right)^2\right]^2 + \frac{4\omega^2\omega_0^2}{\omega_0'^4}}}\right][V_{ac}\cos(\omega t)] \quad \text{(S5)}$$

$\omega$ near $\frac{\omega_0}{2}$ $$= [C_o V_{ac}\cos(\omega t)] - \left[\frac{QC_0'V_{ac}^2}{8k'\sqrt{Q^2\left[1-\left(\frac{2\omega}{\omega_0'}\right)^2\right]^2 + \frac{4\omega^2\omega_0^2}{\omega_0'^4}}}\right]$$

$$[\cos(3\omega t - \phi_2) + \cos(\omega t - \phi_2)]$$

Thus, for $\omega$ near $\omega_o$, the denominator of the second terms in eqns. S3 and S4 becomes small, and q(t) oscillates with large amplitude at $2\omega$, the second harmonic of the applied angular frequency, $\omega$. For $\omega$ near the sub-harmonic $\omega_o/2$, q(t) oscillates with large amplitude at $3\omega$, the third harmonic of the applied angular frequency, as well as at the first harmonic.

As an illustration, if the resonant frequency of a mode is $\omega_0 \approx 20$ kHz, q(t) will have maxima for $2\omega$ near 20 kHz (or $\omega$ near 10 kHz) and for $\omega$ near 20 kHz (cf. eqn. S1). When $\omega$ is near 10 kHz, q(t) will have a large Fourier component near 30 kHz (cf. eqn. S5). When $\omega$ is near 20 kHz, q(t) will have a large Fourier component near 40 kHz (cf. eqn. S4). In both cases, the fundamental of the applied frequency is present without any vibration x(t) of the cantilever, due to parasitic capacitance as well as the first term $C_0 V_{ac}\cos(\omega t)$ in eqns. S4 and S5, so that measuring the charge on the cantilever at the fundamental frequency will not show a large effect at the normal mode frequency.

Thus even in the case when the vibrations of the cantilever are small enough to enable a linear theory, the second and third harmonics should be large. When the vibrations are not small with respect to the distance between the cantilever and the counter electrode, nonlinearities and parametric effects are expected that would increase further the importance of the higher harmonics in q(t), and it is precisely these effects that are of key importance to the present subject matter.

The difference between k and k' (and thus between $\omega_o$ and $\omega_o'$) can be tuned by the applied ac and dc voltages. This effect is not necessarily small, but even when so, because of the large Q factors it is easily observable, even in nanotubes, The electrical forces perturb k to k' by an amount $$\frac{dF_e}{dx}.$$

Now, $$\frac{dF_e}{dx} = \quad \text{S(6)}$$

$$\frac{d\{1/2C_0'(V_{dc}+W)^2 + 2(V_{dc}+W)V_{ac}\cos(\omega t) + \frac{1}{2}V_{ac}^2[1+\cos(2\omega t)]\}}{dx} = -1 \bigg/ 2\left[\frac{d^2C}{dx^2}\right]_{x=0}$$

$$\left\{(V_{dc}+W)^2 + 2(V_{dc}+W)V_{ac}\cos(\omega t) + \frac{1}{2}V_{ac}^2[1+\cos(2\omega t)]\right\}$$

The time dependent terms will average out (but contribute to the higher harmonics), so that the resulting change in the observed frequency is proportional to the second $$[(V_{dc}+W)^2 + 1/2V_{ac}^2].$$

It has been found experimentally (see the following Example section) that there is a decrease in the resonant frequency as $V_{ac}$ is varied (cf. FIGS. 6 and 8), in agreement with this treatment.

In the tip-to-tip configuration, the charges accumulated at the tip of a cantilever and on the counter electrode can be assumed to be quasi point charges, Q, which can be expressed as:

$$Q = \alpha[(W_{Au} - W_{MWNT}) + e(V_{dc} + V_{ac}\cos 2\pi f_E t)]$$

where $\alpha$ is a geometrical factor related to the counter electrode geometry and the charges are separated by a distance R. The Coulomb force, $F_e$, between the charges on the counter-electrode tip and cantilever is given by $$F_e = \frac{1}{4\pi\varepsilon_0\varepsilon_r R^2}Q^2 = \frac{\alpha^2}{4\pi\varepsilon_0\varepsilon_r R^2}[A_{DC} + A_{f_E}\cos 2\pi f_E t + A_{2f_E}\cos 4\pi f_E t]$$

where $$A_{DC} = [(W_{Au} - W_{MWNT}) + eV_{dc}]^2 + e^2\frac{V_{ac}^2}{2};$$

$$A_{f_E} = 2eV_{ac}[(W_{Au} - W_{MWNT}) + eV_{dc}] \text{ and}$$

$$A_{2f_E} = e^2\frac{V_{ac}^2}{2}.$$

For small oscillations, the excitation y of each normal mode can be expressed as a forced oscillator, with linear damping $$b \frac{\partial y}{\partial t}$$

$$m_e \frac{\partial^2 y}{\partial t^2} + b \frac{\partial y}{\partial t} + k_e y = F_e,$$

where the $m_e$, $k_e$ and $F_e$ are the mass, elastic constant and force for an equivalent oscillator driven at frequency $f_E$. When $f_i$ is near $f_E$, the steady state solution for the above equation can be written as:

$$y = \frac{\alpha^2}{4\pi\varepsilon_0\varepsilon_r R^2} \frac{A_{f_E}}{2\pi\sqrt{m_e^2(f_E^2 - f_i^2)^2 + b^2 f_E^2}} \sin(2\pi f_E t - \delta),$$

where the phase shift $\delta$ for the mode with frequency $f_1$ is given by:

$$\delta = \cos^{-1}\left(\frac{b f_E}{\sqrt{m_e^2(f_E^2 - f_i^2)^2 + b^2 f_E^2}}\right)$$

The resonant frequency of the element can be obtained by finding the excitation frequency that matches the natural mode frequency. Note that similar expressions can be obtained for a steady state solution when $f_i$ is near $2 f_E$.

There can also be a charge oscillating at frequency ω induced on the assembly by parasitic capacitances that exist between components of the circuitry, leading to the presence of electronic noise in the generated signal. However, as this is not at resonance, the noise signal will not include any harmonic terms, and thus can be separated from the signal generated due to the resonance of the element through utilization of the harmonic components of the resonant signal.

According to the present invention, the signal generated from the charge induced at resonance, and in particular, the angular frequency, amplitude, and phase of the signal generated, can be detected and analyzed through utilization of the harmonic components of the signal. These components of the signal can be separated from the fundamental mode of the signal and noise due to parasitic capacitance through use of a signal processor such as a lock-in amplifier. For example, and referring again to FIG. 1, down line of the cantilever assembly 10, the device can include an optional low noise amplifier 13 to provide signal enhancement. For instance, a charge sensitive preamplifier, such as the A250 charge-sensitive preamplifier available from the Amptek Corporation of Bedford, Mass., can be placed in the line following the cantilever assembly 10.

Down line from the optional low noise amplifier 13 a signal processor 16 can be located. For example, a lock-in amplifier can be utilized as the signal processor 16. In this particular embodiment, the drive signal provided from the signal generator 12 can be fed to the lock-in amplifier 16, as shown, but the reference signal of the lock-in, rather than being set to the frequency of the generated signal, ω, can be set to a higher harmonic of the generated signal, i.e., 2ω, 3ω, etc. As the signal output from the lock-in can be set so that it represents essentially only frequencies very close to a higher harmonic of the input signal from the amplifier when near resonance, i.e., when ω=ω₀, and the amplitude of this higher harmonic signal can be greater than that of the signal due to noise of the system, the output from the lock-in amplifier can be used to clearly and unambiguously determine the resonant frequency of the cantilever assembly. When the voltage applied to the counter electrode induces the natural resonant frequency of the cantilever, the signal generated at the cantilever can demonstrate that resonance through, for example, greatly increased signal amplitude and phase shift, either or both of which can then be observed at the lock-in amplifier during signal examination for the harmonics of the applied charge.

If desired, the signal sent to the signal processor 16 can be modified from that generated at the signal generator 12. For example, in one embodiment, the signal from the signal generator 12 can be sent into a frequency modifier that can double or triple the frequency of the signal prior to sending the signal into a lock-in amplifier as a reference signal. According to this particular embodiment, the signal provided to the lock-in amplifier on this line can have a frequency identical to a multiple of the frequency of the signal generator, and thus the lock-in will be sensitive to that multiple of the signal applied to the counter electrode. According to this embodiment, a lock-in could be used without the necessity of an internal circuit for measuring the higher harmonics of the resonant frequency.

The methods and systems of the present invention are not limited to utilization of a lock-in amplifier for processing the signal from the assembly 10 and detecting the resonance of the cantilever. It should be understood that any electronic detection system as is known in the art can be utilized according to the presently disclosed methods to detect the higher harmonics that will exist in the signal induced at resonance. For example, in another embodiment, a phase detector can be utilized to detect differences in phase between the signal induced at the cantilever assembly and the signal supplied from the signal generator. Phase detectors may be employed using a circuit that extracts the phase out of the signal induced at the cantilever in real time, similar to the manner in which the frequency of the signal is reconstructed from lock-in outputs. A suitable phase locked loop (PLL) circuit may be used for this purpose. The combination of a PLL and a voltage controlled oscillator may be used to provide feedback that sharpens the resonance and provides a signal proportional to $\omega_0$. In addition, as previously alluded to with relationship to further embodiments of the present subject matter, plural phase detectors may be employed to determine phase and amplitude differences between plural harmonics and the drive signal to obtain additional data. Other techniques may also be employed such as, but not limited to, waveform analysis to determine the plural phase and amplitude relationships. Additionally, the waveform may be analyzed in the time domain, without Fourier decomposition, such as with computer modeling or mathematical simulation of the system. Such a model may be comprised of a mathematical approximation of the electrical circuit and the mechanical properties of the cantilever and its environment.

Beneficially, due to the improved resonance sensing capability, the electrostatic capacitance at the junction of the resonating element with the counter electrode need not be maximized through minimization of the gap distance, as has been the case in previous capacitance-based NEMS and MEMS. As such, the gap distance between the counter electrode and the element can be much larger in the disclosed devices than thought possible in NEMS and MEMS of the past, and resonance can still be easily and accurately determined according to the disclosed method. For instance, in one embodiment, resonant frequency can be determined for nano-sized cantilevers in a system including the cantilever and the counter electrode in a parallel configuration and at gap distance greater than about 1 µm, or greater yet, for example, about 2 µm in some embodiments. When considering systems of the present invention including nano-cantilevers in a tip-to-tip arrangement with the counter electrode, resonance can be induced and detected at gap distances of up to about 200 nm. Systems of the invention incorporating micro-cantilevers can have resonant frequency discerned at gap distances previously considered too large for detection. For instance, resonance can be induced and unambiguously detected in systems in a parallel configuration with a gap distance of greater than about 10 µm according to the presently disclosed methods. The gap distance can be even larger in other embodiments, for instance greater than about 20 µm.

In addition to determining the change in the resonant frequency, sensors of the invention can also detect and analyze the change in the Quality factor (Q-factor) of the element. While not a requirement of the present invention, analysis of the Q-factor can serve as an additional variable to monitor a change in resonant frequency of the element. Particularly high Q-values are possible when utilizing the disclosed devices in a vacuum. For instance in some embodiments of the present invention, Q-values greater than about 10,000 are possible. As is generally known, the Q-value can generally be considered to be equal to the energy of the oscillating element divided by the energy loss to dissipative forces in one cycle. In one embodiment, the disclosed devices can be utilized as chemical sensors.

In one embodiment of the present invention, an element as herein described can be contacted with a gaseous, vaporous, or liquid stream containing a species. According to this embodiment, the device can define a fluid flow field such as a channel or porous web or membrane for flowing a liquid species to the element or a contained line or chamber to encourage the flow of a gaseous or vaporous species to the element. In any case, the fluid flow field can provide direction to a fluid flow such that the fluid that carries the species, be it liquid, gas, or vapor, can interact with the element. For instance, the fluid flow field can contact the element such that the species contained in the fluid can interact with the element through direct contact.

Upon interaction between the species and the element, for example, upon adsorption of the species to a surface of the element, a change in the resonant frequency of the element can occur that can then be detected as herein described. Moreover, this shift can vary in characteristic depending upon the species. Thus, the shift in resonant frequency of the element upon interaction of the species with the element can be utilized to identify the species.

In some embodiments, characteristics of the shift in the resonant frequency can also be proportional to the concentration of the detected species. As such, in certain embodiments, the disclosed sensors can also be utilized to quantify the cause of the shift in charge characteristics, e.g., the concentration of a detected species. For instance, the disclosed systems can be advantageously utilized in recognizing and determining extremely small masses, i.e., as a micro- or nano-balance.

Optionally, sensors of the present invention can be designed so as to bind a particular species of interest. For instance, a semiconductive or conductive cantilever as herein described can be pre-treated so as to preferentially bind an analyte of interest, and the sensor can then be utilized to detect that specific analyte. For example polyclonal or monoclonal antibodies as are generally known in the art could function as a binding agent for an analyte specific to that antibody, such as *Aspergillus niger* spore analytes, for instance. Any suitable method can be utilized to attach the binding agent to a cantilever. For instance, pentaerythritol tetranitrate and hexahydro-1,3,5-triazine, both of which can bind to a silicon microcantilever with its gold surface modified with a self-assembled monolayer of 4-mercaptobenzoic acid, can be utilized to attach the binding agent to a cantilever. In one particular embodiment the disclosed systems and methods can be utilized in biosensing, enabling the detection of extremely small amounts of biological species.

In one embodiment, the present invention can be used to detect species at very low concentrations. For instance, as the disclosed devices can operate in the microwave regime, the presence of species in concentrations as low as parts per billion can lead to a discernable shift in the resonant frequency of the device.

The devices and electronic detection regimes of the present invention can be utilized in many applications in addition to species sensing applications such as those described above. For instance, the disclosed methods and devices can be utilized in applications directed to detecting changes in the surrounding atmosphere. For example, the devices can be used to detect changes in surrounding pressure, such as those due to atmospheric change or atmospheric acceleration, changes in surrounding magnetic forces, or changes in temperature. Moreover, and similar to the species sensing applications described above, characteristics of the shift in the resonant frequency can also be proportional to the strength of the environmental change causing the shift. Accordingly the sensors can be utilized to quantify the environmental changes leading to the shift in resonant frequency of the element.

In one embodiment, the devices and regimes disclosed herein can be utilized to detect an alteration in a species due to a particular environmental condition, and thereby can be utilized to detect the environmental condition. For example, a species that will undergo characteristic change in the presence of an environmental condition can be isolated with a sensor as described herein. Following exposure to the environmental condition, the characteristic change in the species can be reflected in a change in the resonant frequency of the device. Hence the existence of the underlying cause of the change, i.e., the environmental condition, can be established. For instance, upon exposure to radiation, many known species can undergo a characteristic change that can lead to a discernable shift in the resonant frequency of a sensor near the species.

Figure 15:
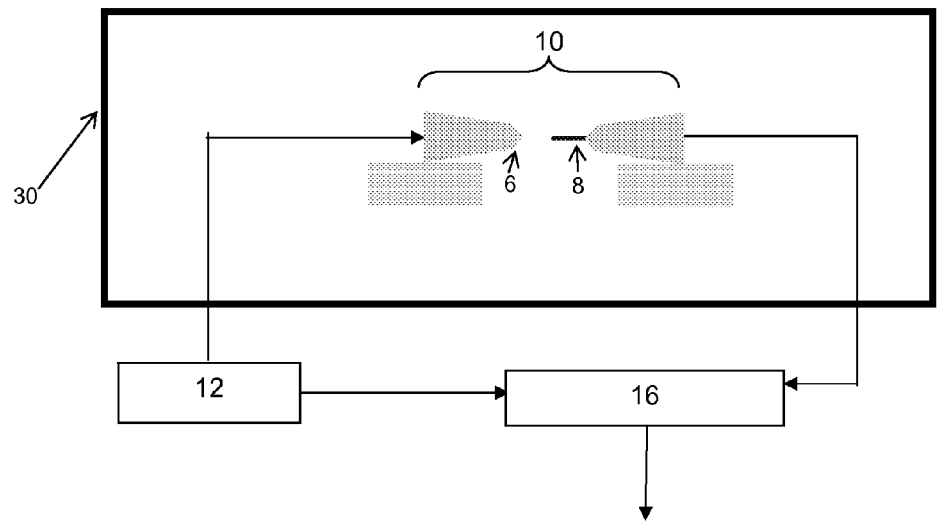
FIG. 15 schematically illustrates a sensor according to one embodiment of the present invention.

One specific embodiment of such a system is schematically illustrated in FIG. 15. As can be seen, a cantilever assembly 10 can be isolated in a chamber 30. For instance, the chamber 30 can be a vacuum chamber partially filled with a species, such as argon. In the presence of radiation, the argon atoms can be ionized, and be electrostatically attracted towards the cantilever 8. This can result in a shift in the resonant frequency of the cantilever 8 that can be monitored and detected as described above.

The systems of the present invention can also be beneficially incorporated into other devices as well. For example, the capability of direct electronic determination of the resonance of a micro- or nano-sized cantilever can be beneficially incorporated into any device that can employ cantilever-based NEMS or MEMS. The disclosed methods can beneficially be utilized in formation of switching devices, electronic sending/receiving devices, or any NEMS or MEMS device based upon the use of dynamic capacitance or electrostatic actuation and detection.

In one embodiment, the methods and devices disclosed herein can be utilized in sensing/imaging techniques such as atomic force microscopy (AFM). One embodiment of an AFM according to the present invention is illustrated in FIG. 16. As can be seen with reference to the Figure, a cantilever 8 can be electrostatically driven to oscillate at its resonant frequency due to the electrostatic force of a voltage applied to counter electrode 6 via a signal from signal generator 12. The resonance of the cantilever 8 can be determined and monitored as described above through utilization of a suitable signal processor 16, such as a lock-in amplifier. In addition, the cantilever 8 can be in mechanical communication with an AFM arm 20 that is capable of motion and controlled with AFM system 22 as is generally known in the art. During use, the location and motion of AFM arm 20 can be controlled in response to signal information obtained from the signal processor 16, as shown. As the cantilever approaches a sample held on stage 25, atomic forces between the cantilever 8 and the sample can cause a changes in the resonant frequency of the cantilever. A feedback loop between the signal processor 16 and the AFM arm 20 can adjust the height of the cantilever 8 over the sample in order to keep the cantilever 8 at resonance. Information concerning the height of the AFM arm 20 at resonance can then be collected to create data points by the AFM system 22. As data points are taken and recorded as the cantilever 8 scans the sample, a topological image of the sample can be developed according to standard AFM imaging methods as are generally known in the art. The AFM system can optionally work in non-contact or tapping mode, as desired.

The disclosed AFM systems may provide additional benefits over more traditional AFM systems when operating in tapping mode. For example, in one embodiment, as discussed above, the cantilever of the disclosed systems can include one or more carbon nanotubes. Carbon nanotubes are understood to be less fragile and more elastic than traditional AFM tips, such as those formed of silicon or silicon nitride. Accordingly, AFMs as herein described can be more resilient than previously known AFM systems, and the disclosed systems can be utilized with less down time due to probe damage and replacement as compared to more traditional systems.

In other embodiments, the disclosed devices can be utilized as switching devices, antennas, or any other device that can take advantage of the direct electronic detection of the change in amplitude and phase of the element upon a change in the resonant frequency of the element.

In accordance with further embodiments of the present subject matter, rather than detecting only the frequency, amplitude, and/or phase of the resonance or a harmonic of resonance of the microcantilever oscillating in an applied electric field, the signal output may be measured and acquired as a electrical waveform, from which the associated mechanical waveform may be derived by applying an appropriate correction function. For example, when a Fourier analysis is performed on the mechanical waveform from a microcantilever oscillating in a nonlinear electric field or with nonlinear or complex damping, it will show more than one frequency component. These frequencies are integer multiples of the natural frequency of the microcantilever, and are called harmonics. Therefore, the nonlinear mechanical waveform can be represented by a superposition of sine waves, each having an integer multiple of the natural frequency of the microcantilever. In accordance with this further embodiment of the present subject matter, an AC and/or DC drive signal(s) may be applied to the cantilever in either a continuous mode or in a pulse or ringdown mode, and either of these methods are capable of producing non-linear oscillations, because of the presence of the nonlinear electric field.

In a continuous mode the microcantilever may be driven by time-invariant AC and DC signals which may have a DC component at or near the natural frequency of the microcantilever. The frequency of the AC signal may be scanned or constant. The electrical output caused by the oscillatory circuit is detected and measured while the AC signal is driving the microcantilever in the nonlinear field resulting from the applied DC voltage.

In a pulse or ringdown mode the microcantilever is driven by a pulsed AC signal which may have a DC component at or near the resonant frequency of the microcantilever. During the 'on' time of the AC signal, the microcantilever is driven. During the 'off' time of the AC signal, the microcantilever is allowed to freely oscillate in the nonlinear field resulting from an applied DC voltage. Due to either intrinsic damping or environmental damping effects, or both, the microcantilever oscillation decays, or decreases in amplitude until the next 'on' pulse of the AC signal. The electrical output from the oscillatory circuit is detected and measured only while the microcantilever is not being driven, i.e. during its decay/ringdown.

In the instance of a constantly driven microcantilever, the output waveform is substantially identical from cycle to cycle. In the case of a pulsed microcantilever, the output waveform, measured during the ringdown, has decaying amplitude. In both cases the waveform contains information relating to the frequency or frequencies of the oscillatory motion of the microcantilever at its natural resonance and its higher harmonics and modes of vibration. The phase and amplitude of each of the output frequencies may be measured either with respect to the driving signal or one another.

The measured electrical output is produced by the oscillatory change in capacitance values between the microcantilever and the counter electrode. For example, any change in the position of the microcantilever with respect to the counter electrode changes the capacitance of the circuit, and can be detected as a change in voltage. When the applied AC voltage causes the microcantilever to move back and forth, an oscillating capacitance is produced which can be measured. In accordance with this embodiment of the present subject matter, direct measurement of this oscillating capacitance is acquired as a waveform for later analysis. It should be appreciated, however, that other methodologies may be applied to detecting the oscillatory changes between the microcantilever and the counter electrode to produce a signal representative thereof such as by employing laser measurement of the distance between the microcantilever and the counter electrode.

Certain characteristics of the electric field between the microcantilever and counter electrode are significant for this embodiment of the present subject matter. For example, there exists a voltage between the counter electrode and the microcantilever that produces an inversely proportional attractive force between the two, i.e., the force increases as the distance between the two decreases and decreases as the distance between the two increases.

By choosing certain geometries of either or both the counter electrode and cantilever, the relation between the attractive electric force and the separation between the two may be made more nonlinear. For example, by choosing a small diameter sharpened tungsten wire as the counter electrode, the nonlinearity of the electric force may be increased. Other geometries may be realized and may increase or decrease the nonlinearity of the electric force. As previously noted, for example, plural counter-electrodes may also be employed.

As the oscillating microcantilever moves closer to the counter electrode in a half cycle, it experiences an increased attraction to the counter electrode. Thus, the mechanical amplitude during that half cycle is larger than it would be outside the influence of the attractive force. In addition, the attractive force causes the microcantilever to linger in the vicinity of the counter electrode longer than normal. This effect is manifested as a decreased frequency of oscillation for that half cycle, called spring softening. As the oscillating cantilever moves away from the counter electrode in a half cycle, it experiences a decreasing attraction to the counter electrode. However, there still exists an attractive force on the microcantilever. Thus, the mechanical amplitude for this half cycle is less than it would normally be without the influence of the attractive force. In addition, for this half cycle, the attractive force causes the microcantilever to cease its motion away from the counter electrode sooner than it normally would outside the influence of the attractive force, causing an increased frequency of oscillation for that half cycle, called spring hardening. Since in a nonlinear field, the attractive force is greater when the microcantilever is closer, the net effect is a decrease in its frequency of oscillation, or a net spring softening. This process is illustrated generally in FIG. 20. as will be described further later with respect to Example 6.

Since the mechanical motion of the microcantilever in each half cycle is affected by the nonlinear electric field by differing amounts, the resulting waveform created by tracing the microcantilever motion in time is perturbed from a sinusoidal harmonic shape. For a microcantilever continuously driven by an AC signal at or near resonance in a nonlinear electric field, the resulting nonlinear output mechanical waveform will appear as a repeating series of substantially identical non-sinusoidal cycles. In the case of a microcantilever driven to resonance and then released to resonate freely, damping effects will cause a decrease in the amplitude of the output waveform over time. Since in this case, as the mechanical amplitude decreases, the variation of the force applied during a cycle is reduced, the perturbation of its motion due to the nonlinear field is not as great. Thus, with increasing time, the spring softening will lessen, yielding a more nearly linear sinusoidal motion and a frequency increase.

If a Fourier analysis on the mechanical waveform resulting from a microcantilever oscillating in the described nonlinear electric field is conducted, it will show more than one frequency component. These frequencies are harmonics, i.e., integer multiples, of the natural frequency of the microcantilever. Therefore, the nonlinear mechanical waveform can be represented by a superposition of sine waves, each having an integer multiple of the natural frequency of the microcantilever.

Though the microcantilever motion is mechanical, the output from the entire system is electrical, since the measured electrical output is a result of the changing voltage due to the changing capacitance between the microcantilever and the counter electrode(s). Thus, the true mechanical motion of the microcantilever is buried in the electrical output, also a waveform. Since the dimensions and geometry of the counter electrode and cantilever can be chosen to maximize electrical nonlinearities, the electrical output waveform of even a perfectly sinusoidal mechanical oscillation of the microcantilever will still show electrical nonlinearities in the waveform in the form of higher harmonics. A key advantage to detecting the mechanical motion of the microcantilever electrically is that the electrical signal output gives a nonlinear signal amplification of the mechanical motion, yielding significant sensitivity to changes in the mechanical motion.

The nonlinear electrical waveform output acquired in accordance with the present subject matter can be mathematically approximated by considering all of the forces acting on the microcantilever arising from electrical and mechanical sources. Electrical forces may be represented by the AC field (in the case of a continuously driven microcantilever) and the applied DC field, with nonlinearities caused by the geometry of the electrode(s) and cantilever. Examples of mechanical forces acting on the cantilever are the restoring force of the microcantilever itself, intrinsic dissipative losses due to the internal structure of the microcantilever, and external damping forces caused by environmental conditions such as surrounding gases having linear and nonlinear viscosity and density or nearby surfaces having attractive or repulsive forces due to electrostatic or van der Waals interactions. If the mathematical approximation of all the forces acting upon the microcantilever is a good one, the electrical output waveform can be fitted closely and the forces identified and/or deconvoluted.

In accordance with the present subject matter, significant and important differences have been identified between a damped sinusoidal oscillator and one that is vibrating nonlinearly such as in this embodiment of the present technology as follows. Firstly, a sinusoidal oscillator has only one frequency of vibration, independent of amplitude. A nonlinear oscillator as per present technology may have several frequencies of vibration as in a Duffing oscillator. In the present case, those frequencies are at integer multiples or harmonics of the natural frequency and each of these frequencies has an independent amplitude.

Secondly, the single frequency of the sinusoidal oscillator remains constant in time. A nonlinear oscillator outputs a waveform that has a varying frequency based on amplitude. In accordance with a third difference, the decay in amplitude of the single frequency of a damped harmonic oscillator describes a single function that is directly related to the total damping on that oscillator. The decay in amplitude of each of the frequency components in a nonlinear oscillator describes several independent functions which are not all directly related to the total damping on the oscillator.

Finally, the phase of the sinusoidal waveform output from a linear sinusoidal oscillator remains constant independent of amplitude. In accordance with present technology, however, the phases and amplitudes of each of the frequency components of a nonlinear oscillator change with the total mechanical amplitude and with respect to one another. These changes in phase can be described as independent functions of each frequency phase.

Taken as a whole, for any system, a perfectly sinusoidal oscillator output waveform consists of an amplitude, single frequency, and phase, all of which are directly related to one number, i.e., the total damping on that system. The output waveform of a nonlinear oscillator, on the other hand, can be broken down into several components which can be thought of as a measurement of several numbers which are independent of one another. These numbers correspond to the amplitudes or amplitude functions of each of the frequencies or harmonics considered independently or with respect to one another; the phases or phase functions of each of the frequencies or harmonics considered independently or with respect to each other; and the change in frequency of each of the frequencies or harmonics as a function of amplitude. This embodiment of the present subject matter takes advantage of these multiple data points to obtain improved resolution with respect to monitored systems.

It should be appreciated that the various embodiments of the present technology may be implemented and employed to determine characteristics of known environments whereby libraries of measurements obtained through the use of present technology may then be used to evaluate unknown environments.

The various embodiments of the present subject matter may be more clearly understood with reference to the Examples, below. All measurements in all Examples were performed in air under ambient conditions unless otherwise noted.

EXAMPLE 1

Figure 2:
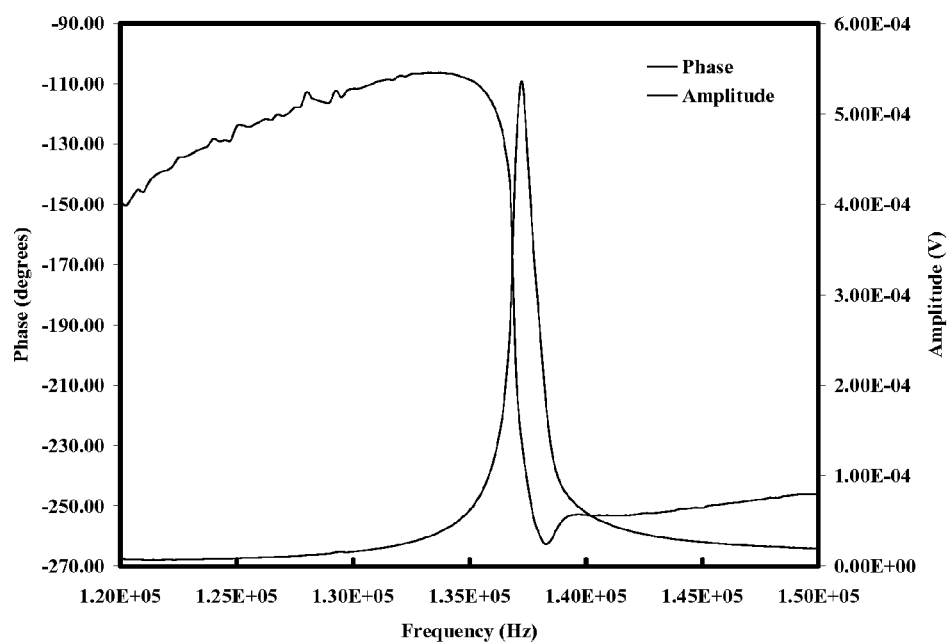
FIG. 2 graphically shows the amplitude and phase changes with regard to frequency of applied voltage for an exemplary system of the present invention including a silicon microcantilever.

A system similar to that illustrated in FIG. 1 was developed including a silicon micro-cantilever approximately 100 μm in length. A modulated ac charge was applied to the counter electrode at varying frequencies. The signal generated at the cantilever was analyzed at a lock-in amplifier using the second harmonic where both amplitude and phase were determined. Results are illustrated in FIG. 2. As can be seen, the resonant frequency can be clearly recognized by both an increase in frequency amplitude and phase shift.

EXAMPLE 2

Figure 3:
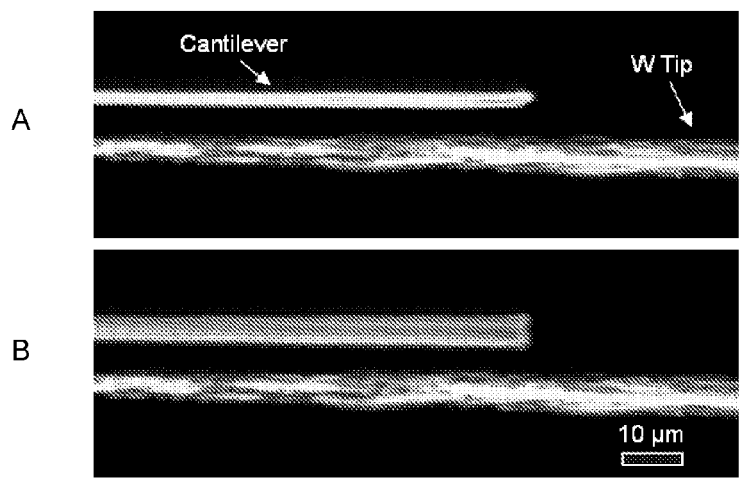
FIG. 3 is a dark field image of a parallel configuration of a micro-silicon cantilever that can be utilized according to the present invention in which the cantilever is at rest in FIG. 3A and vibrating in FIG. 3B.
Figure 4:
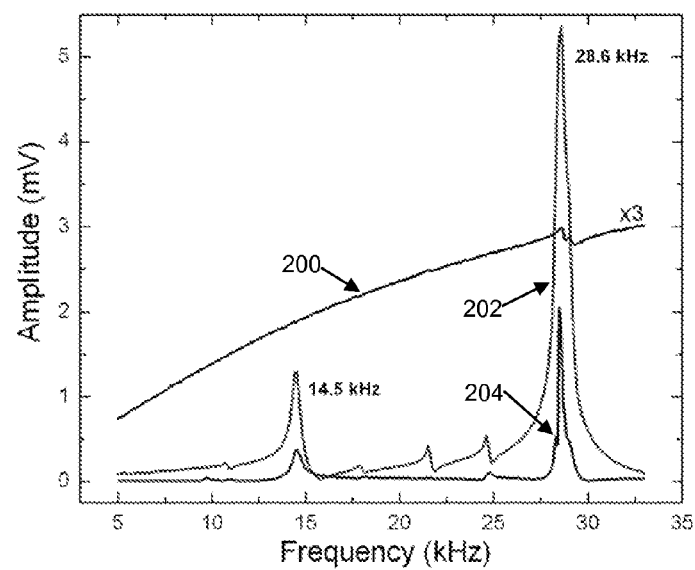
FIG. 4 graphically illustrates data obtained via one embodiment of the disclosed system.

A system such as that illustrated in FIG. 1 was constructed utilizing a commercially available tipless aluminum coated silicon cantilever with known fundamental modes (300 μm long, 35 μm wide, and 2 μm thick, available from MikroMasch) that was placed in parallel arrangement with a counter electrode, as shown in FIG. 3. In separate runs, the lock-in amplifier was set to measure the driving frequency, the second harmonic, and the third harmonic, respectively. The results are shown in FIG. 4, lines 200, 202, 204, respectively. As can be seen, when the lock-in was set to measure at the driving frequency, the weak signal generated from the movement of the cantilever at resonance was measured as a small peak riding the broad signal present, due to the parasitic capacitance. In addition, and as expected, the baseline when looking for the $1^{st}$ harmonic gradually increased with the frequency. Although there was a response at the resonant frequency, the signal to noise ratio (S/N) was very small. When this signal was instead detected at the second harmonic, the signal stemming from the parasitic capacitance was avoided, which permitted the detection of the resonant frequency ($\omega_o$) with a superior S/N. Weak peaks present between $\omega_o/2$ and $\omega_o$ were believed to be due to residual electrical pick-up, as they did not respond to changes in the applied ac or dc voltage. In addition, it was found that measuring in the $3^{rd}$ harmonic a higher Q-value was obtained than when measuring in the second. Accordingly, in some embodiments of the disclosed invention, it may be preferred to detect the resonant frequency of the cantilever via the $3^{rd}$ or even higher harmonics.

Figure 5:
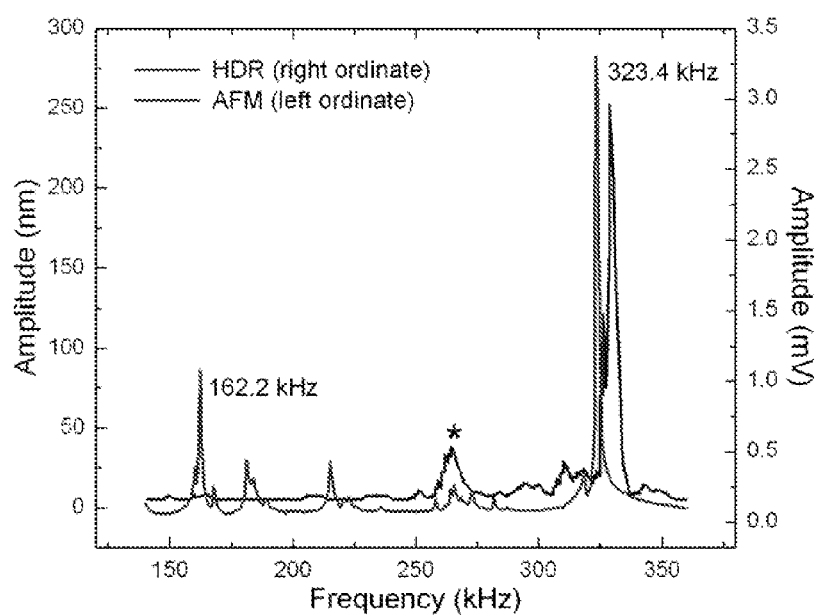
FIG. 5 compares the resonant frequency data for a silicon micro-cantilever obtained via the disclosed methods to that of the same cantilever obtained via an AFM optical technique.

FIG. 5 compares the resonant frequency obtained for a similar micro-cantilever system (cantilever dimensions were 90 μm long, 35 μm wide, and 2 μm thick) according to the disclosed methods to that determined from a well established optical technique which is routinely used utilizing an atomic force microscope (Veeco di-CP II). The agreement between the measurements is a further indication of the efficacy of the presently disclosed techniques. The small differences in the resonant frequencies are attributed to differences in the excitation methods (piezoelectric vs. the disclosed direct methods). A quality factor Q=200 was obtained for the $2^{nd}$ harmonic detection of the fundamental mode frequency.

As can be seen, with reference to the Figures, the cantilever also vibrated when the oscillator applied a signal with frequency $\omega=\omega_o/2$. When the resonance spectrum was obtained with the AFM, the excitation was applied by a piezoelectric source, and hence no peak at $\omega_o/2$ was seen. As expected, the $1^{st}$ harmonic signal was small, and the $2^{nd}$ and $3^{rd}$ harmonic signals gave a clear indication of the resonance.

Figure 6:
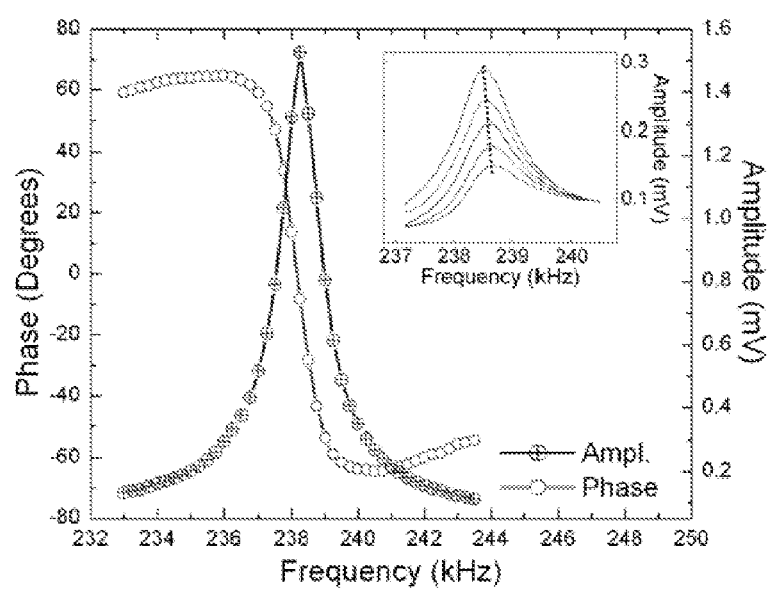
FIG. 6 illustrates the resonance spectra data for another silicon micro-cantilever.

In a separate measurement, the resonance spectrum and phase for a similar silicon micro-cantilever (110 μm long, 35 μm wide, 2 μm thick) was determined according to the present process. FIG. 6 shows that the amplitude peak is accompanied by a phase change of ~130°. It should be emphasized that according to the presently disclosed methods, the amplitude and phase can be determined simultaneously. The inset of FIG. 6 illustrates the weak dependence between the natural resonant frequency of the system and the applied ac voltage. This softening is believed to be due to a decrease in the effective spring constant of the system induced by the applied voltage.

EXAMPLE 3

Figure 7:
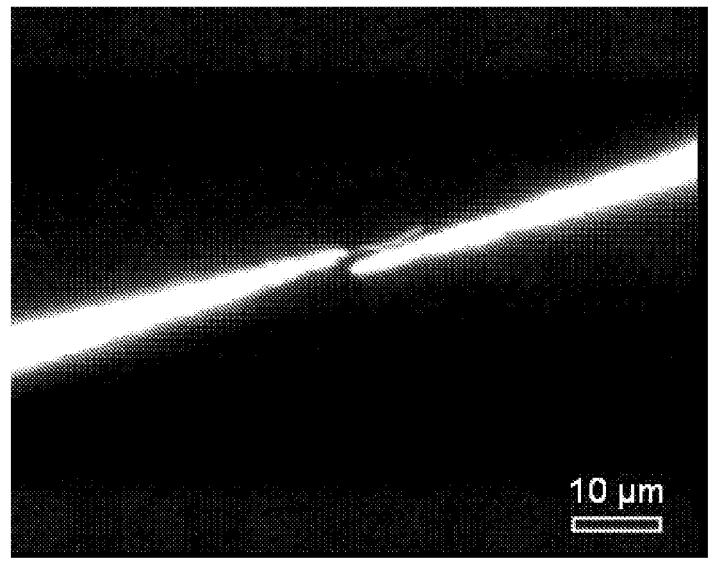
FIG. 7 is a dark field image of a MWNT nano-cantilever in parallel arrangement with a counter electrode.
Figure 8:
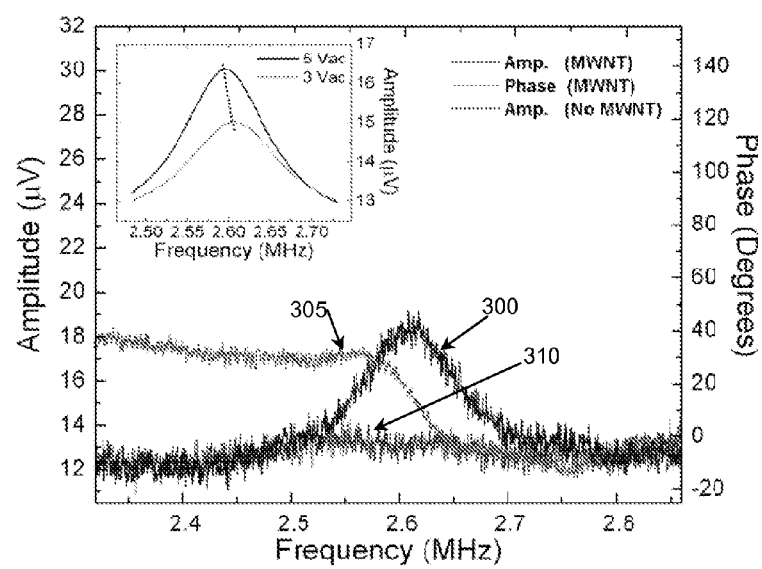
FIG. 8 displays the resonance and phase spectra for a system of the present invention including a MWNT nano-cantilever in a parallel configuration.

The resonant frequency and phase for a cantilevered MWNT was determined. A MWNT (7 μm in length, 50 nm in diameter) was mounted on a sharpened gold-coated tungsten probe and manipulated ~1 μm away from and parallel to the same gold-coated tungsten counter electrode used for Example 2. The MWNTs used in this study were grown by a chemical vapor deposition method (as further described in "Gaillard, J., Skove, M. J. & Rao, App. Phys. Lett. 86, 233109-233109-3 (2005)" incorporated herein by reference) utilizing a two-stage thermal CVD reactor consisting of a low-temperature (~200° C.) preheater followed by a higher-temperature furnace (~750° C.). Typical flow rates of the gases are 200 sccm (standard cubic centimeters per minute) for hydrogen and 675 sccm for Ar. In particular, the MWNTs were prepared from a catalytic decomposition of a trimethylamaine [$(CH_3)_3N$]-ferrocene (TMA/ferrocene) mixture. The MWNTs were determined to have an average diameter of ~50 nm. FIG. 7 is a dark field image of a MWNT cantilever in parallel arrangement with the counter electrode. FIG. 8 displays typical frequency (line 300) and phase (line 305) spectra obtained for the MWNTs when the system was set to ascertain the presence of the second harmonic of the drive signal in the generated signal. For comparison, the resonance spectrum was also collected in the absence of the MWNT for the same tungsten probe geometry (FIG. 8, line 310). Similar to the Si micro-cantilever of Example 2, an accompanying change in phase of about 50° was observed. This phase change value is reasonable due to the presence of noise.

EXAMPLE 4

The harmonic charge modulation detection regime of the present invention was used to measure the mechanical resonance of a single MWNT. A system similar to that shown in FIG. 1 was utilized in which the cantilever was a MWNT placed on a sharpened gold-coated tungsten probe tip. A similar probe tip was used as the counter electrode and aligned with the MWNT in a tip-to-tip arrangement as shown in FIG. 9. The alignment of the MWNT with the counter electrode was monitored using a dark field optical microscope (Nikon Epiphot 200) equipped with a digital camera (MOTICAM 1000). Both an ac voltage and a dc voltage were used to induce charge on the MWNT. The modulated charge on the MWNT was detected and amplified by a low noise charge amplifier (Amptek A250). The output signal of the LNA was detected using a lock-in amplifier set for $2^{nd}$ harmonic detection. A computerized data acquisition system collected the excitation frequency provided by the signal generator, as well as the amplitude and phase of the LNA output signal as measured by the lock-in amplifier.

Figure 10:
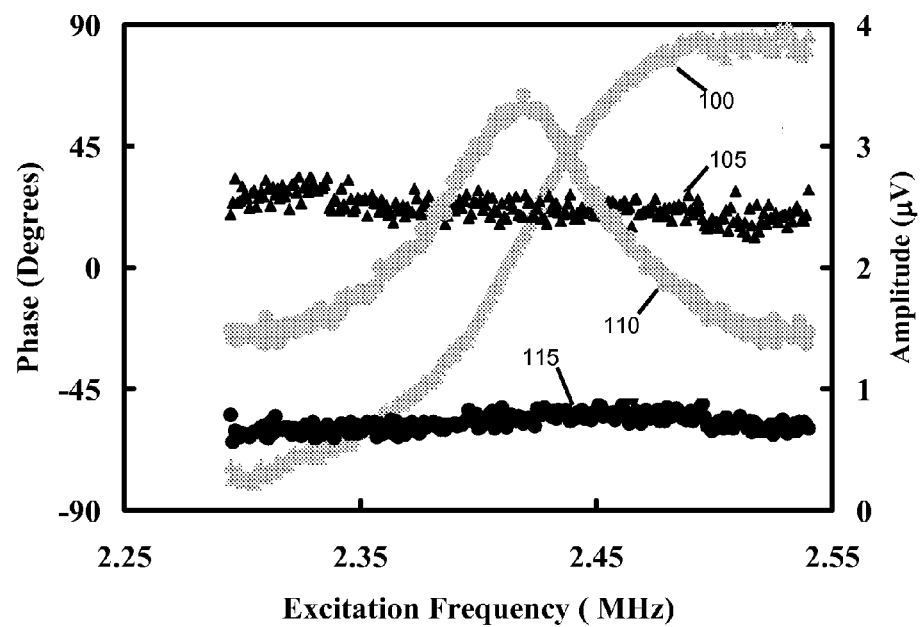
FIG. 10 shows resonance spectra data obtained for a MWNT nanocantilever according to the presently disclosed methods in the tip to tip geometry.

FIG. 10 shows the resonance spectra (phase line 100, amplitude line 110) obtained for a TMA/ferrocene CVD grown MWNT with length of 10 µm, inner diameter 17 nm, and outer diameter 57 nm. The initial gap distance ($V_{ac}=V_{dc}=0$) was estimated to be about 200 nm. As can be seen with reference to the Figure, line 100 shows an associated 160° change in phase at resonance. The maximum amplitude and phase change occurred when the exitation frequency reached 2.420 MHz, which, in this case, was the resonance at the second mode of vibration, as the lock-in was set for the $2^{nd}$ harmonic detection. For comparison, amplitude (line 115) and phase (line 105) signals were obtained for the same geometry of the electrodes in the absence of the MWNT. As can be seen, no noticeable changes in the traces for the amplitude and phase can be discerned in the frequency range between 2.250 to 2.550 MHz when the MWNT was absent.

EXAMPLE 5

The system of Example 4 was utilized, but with a gap distance between the MWNT tip and the counter electrode tip greater than that of Example 4. The second gap distance was estimated to be less than about 400 nm.

Figure 11:
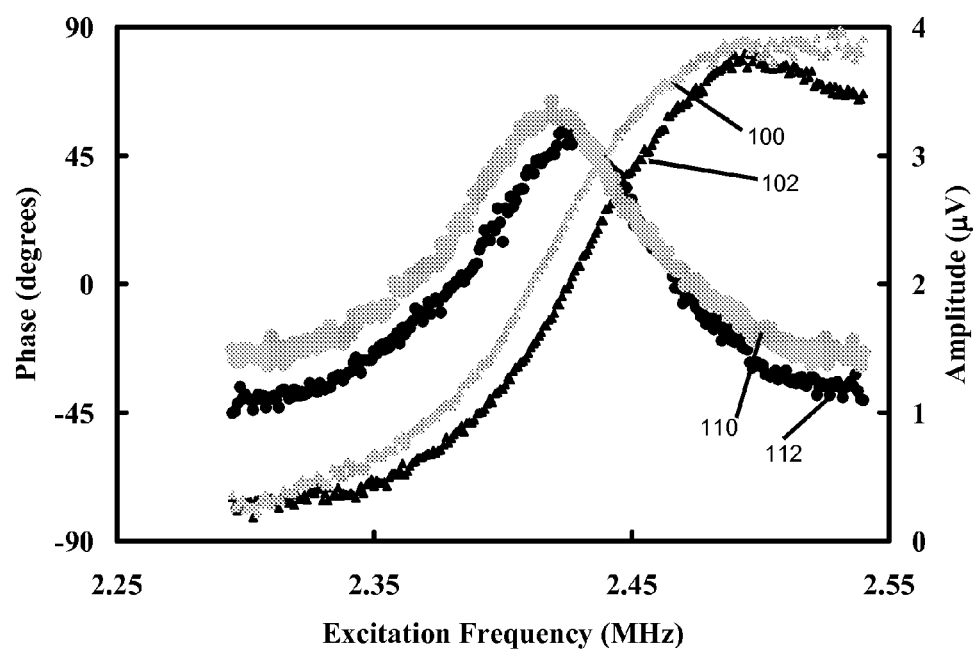
FIG. 11 compares resonance spectra for the MWNT nano-cantilever of FIG. 10 at two different gap distances in the tip to tip geometry.

FIG. 11 illustrates the resonance spectra (phase line 100, amplitude line 110) obtained for the system of Example 4 overlaid with the response of the same system at the greater gap distance (phase line 102, amplitude line 112).

The frequency at maximum amplitude was observed to increase with gap distance from 2.420 MHz to 2.425 MHz, which is clear evidence for parametric excitation. In particular, the slight increase in the frequency at maximum amplitude when the gap distance was increased confirms that the data shown in FIGS. 10 and 11 corresponds to a mechanical resonance of the cantilevered MWNT, since the increase in the measured resonant frequency can be traced to a decrease in the effective electrostatic forces. (As described by Sarid D. *Scanning Force Microscopy with applications to electric magnetic and atomic forces*" Oxford University Press: New York Oxford, 1991.) In addition, the phase change remains constant with increase in gap distance, as would be expected, and the quality factor Q decreased from 37 to 31 when the gap was increased.

The Young's modulus, Y, for the MWNT was also computed from the data using a multi-step procedure.

For a MWNT clamped at one end, the frequency of the $i^{th}$ mode of vibration is given by:

$$f_i = \frac{\beta_i^2}{8\pi} \frac{1}{L^2} \sqrt{\frac{(D_o^2 + D_i^2)Y}{\rho}},$$

where L is the tube length, $D_o$ and $D_i$ are the outer and inner tube diameters respectively. $\rho$ is the density of the MWNT and the $\beta_i$'s were determined from the boundary conditions to be $\beta_1=1.875$; $\beta_2=4.694$; $\beta_3=7.855$. According to the present invention, it is possible to measure the bending modulus of the nanotube. Moreover, as long as the nanotube does not change its geometry by buckling or any other such deformation, the bending modulus will be equal to the Young's modulus. (For additional discussion, see "Gaillard, J., Skove, M. J. & Rao, *App. Phys. Lett.* 86, 233109-233109-3 (2005)" previously incorporated herein by reference.) The geometric parameters for the MWNT investigated here were determined from SEM images to be: L=10 µm, $D_o$=57 nm and $D_i$=17 nm, as described above. In addition, the density of the MWNT was determined (via methods described by Lu Q.; Keskar G.; Ciocan R.; Larcom L. L.; Rao A. M NT05: *Sixth International Conference on the Science and Application of Nanotubes*, 2005, Gothenburg, Sweden 426, which is incorporated herein by reference) to be $\rho=2100$ Kg/m³.

Figure 12:
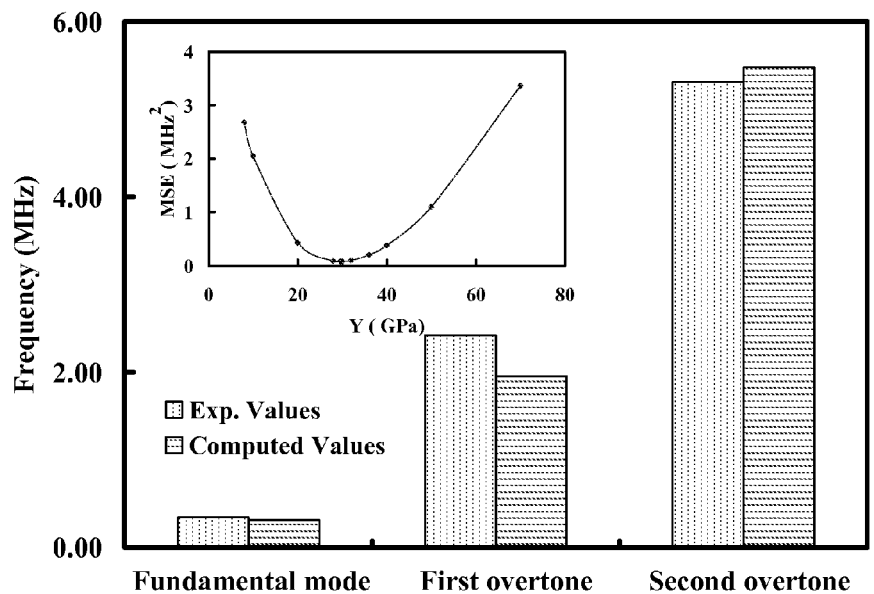
FIG. 12 illustrates the calculated fundamental, $1^{st}$, and $2^{nd}$ overtone modes for a system obtained from the multi-step Young's modulus calculations described in Example 5 and compares those results to the results obtained experimentally according to the presently disclosed process for the first three oscillation modes of a MWNT nano-cantilever.
Figure 13:
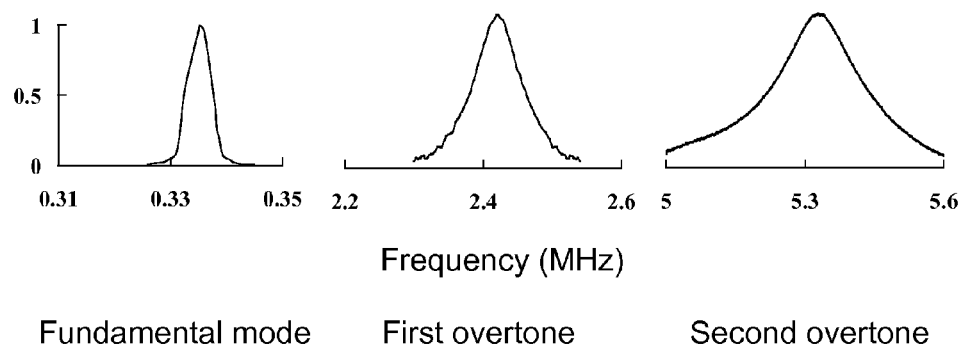
FIG. 13 graphically illustrates the measured amplitude for the fundamental, first, and second overtones in a system including a MWNT nano-cantilever.

The first three oscillation modes of the MWNT were identified from the amplitude and phase changes shown in FIGS. 10 and 11. The experimentally determined resonances were found at $f_{1e}$=0.339 MHz, $f_{2e}$=2.42 MHz and $f_{3e}$=5.31 MHz, as shown in FIGS. 12 and 13. At each step of the multi-stop procedure, the $f_i$'s were computed using the equation above starting with the measured values for $D_o$, $D_i$ and L and a range of values for Y. Then the mean squared error (MSE) for a particular Y was computed as:

$$MSE = \frac{1}{3}\sum_{i=1}^{3}(f_i - f_{ie})^2$$

Figure 14:
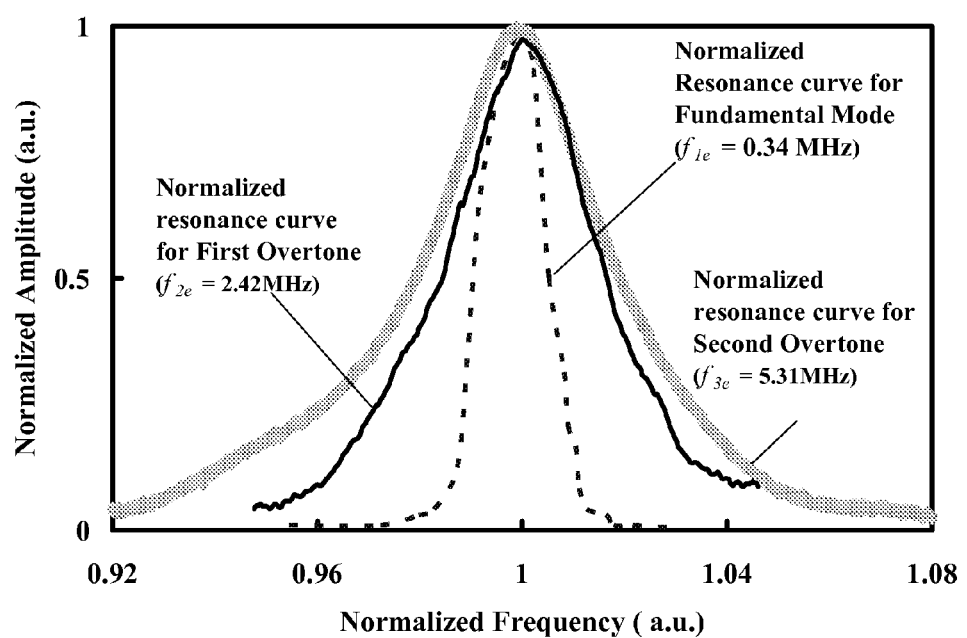
FIG. 14 illustrates the data of FIG. 13 on a normalized frequency scale.

As the inset in FIG. 12 shows, a minimum in MSE for Y=29.6 GPa was found. The values of L and $D_o$ were then perturbed by about ±10% and the minima in MSE recomputed to offer assurance that the minimum was global rather than local. A comparison between experimentally determined frequencies and computed values for Y=29.6 GPa is also shown in FIG. 12. The average error in frequency estimation was about ~10% (ranging from 18% for the first overtone to 3% for the second overtone). The determined value for the Young's modulus Y=29.6±2.9 GPa is in excellent agreement with those reported in the literature for MWNTs with comparable dimensions. The quality factor for each of the three resonances was determined to be 67, 36 and 25 for the fundamental and first two overtones respectively, as illustrated in FIG. 14.

EXAMPLE 6

Figure 17:
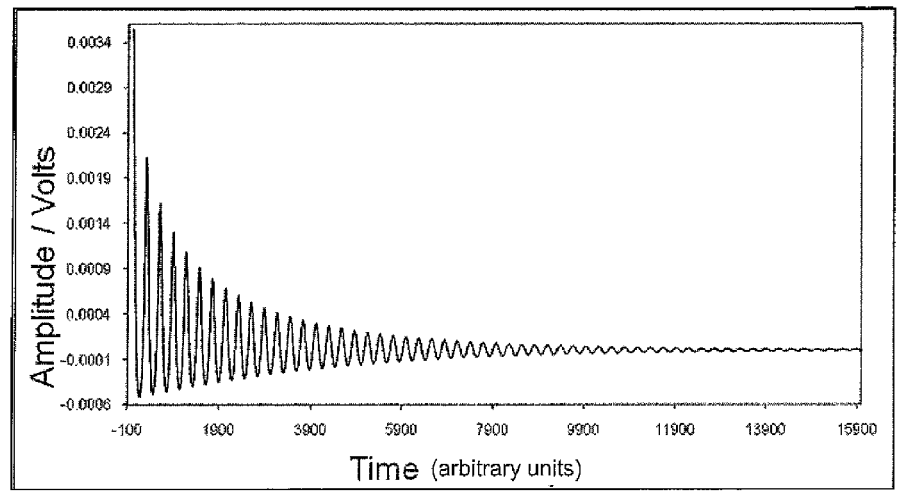
FIG. 17 is a graph of an electrical waveform measured between the element and counter electrode in a second exemplary embodiment of the present subject matter.
Figure 18:
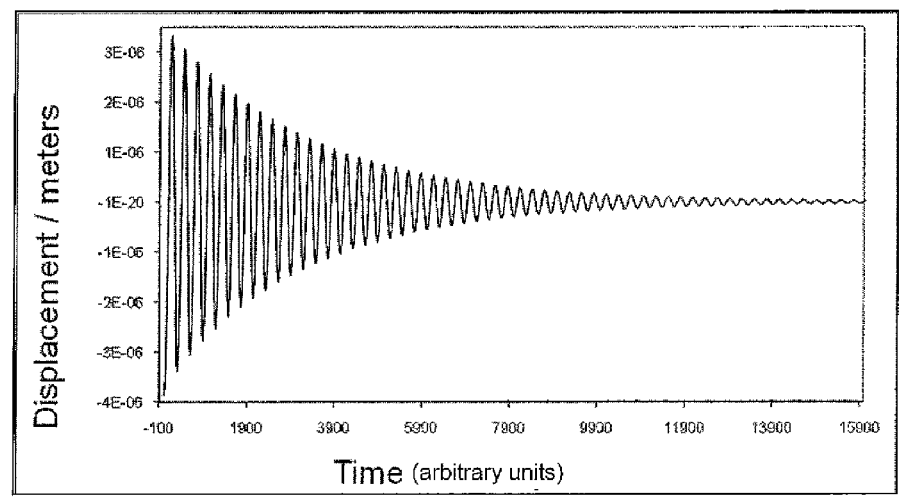
FIG. 18 is a graph of the mechanical displacement of a cantilever element of the second embodiment of the present subject matter having the measured voltage illustrated in FIG. 17.
Figure 19A:
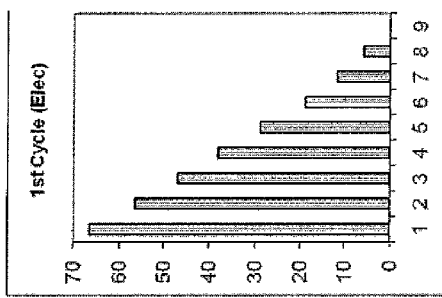
FIGS. 19A-19F graphically represent comparisons of nonlinearity in electrical and mechanical waveforms obtained in accordance with the second exemplary embodiment of the present subject matter.
Figure 19B:
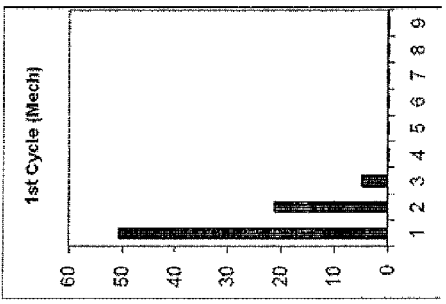
Figure 19C:
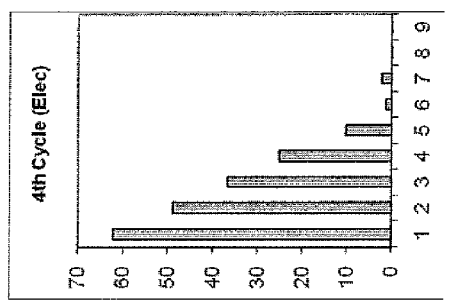
Figure 19D:
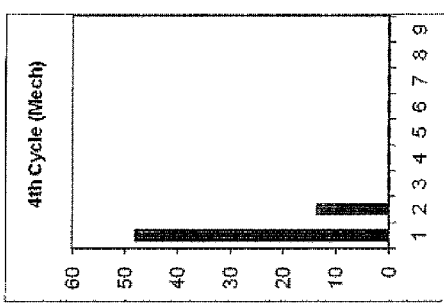
Figure 19E:
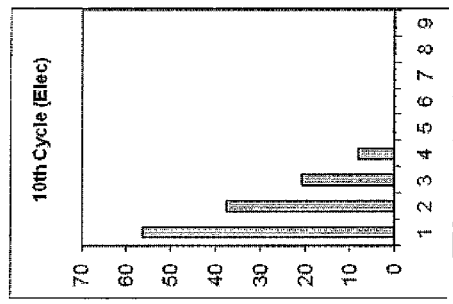
Figure 19F:
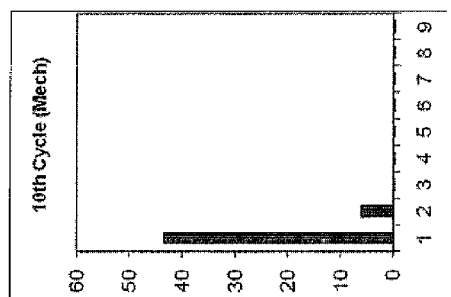
Figure 20:
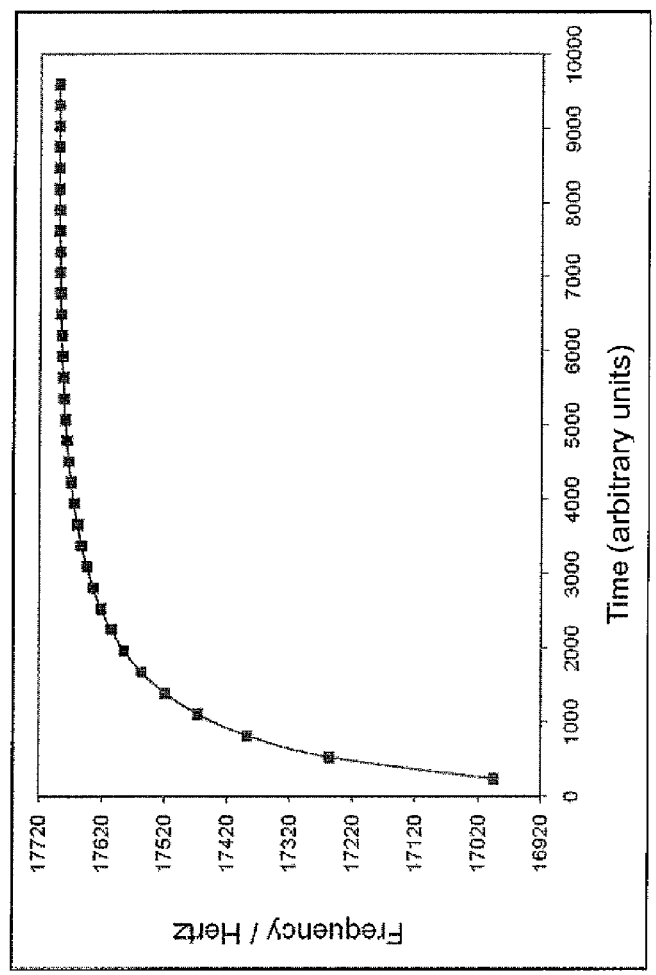
FIG. 20 is a graphical representation of the decrease in spring softening effect (frequency shift) during microcantilever ringdown of an element.

A gold-coated silicon microcantilever was operated in nonlinear pulse-ringdown mode in a setup in accordance with an alternate embodiment of the present technology at the same pressures of deuterium and helium gas. For deuterium, an electrical waveform was acquired and approximately fitted with a mathematical model accounting for all electrical forces on the microcantilever. The electrical output is shown in FIG. 17. From the model, the actual mechanical waveform representing the microcantilever displacement was extracted as illustrated in FIG. 18. The amplification of the mechanical waveform by the electrical circuit is evident in the additional nonlinearity in the electrical waveform. FIGS. 19A-19F show a Fourier analysis of both the electrical and mechanical waveforms at the first, fourth, and tenth cycles. The electrical amplification of the mechanical nonlinearities is evident here as well. As the mechanical oscillation displacement amplitude decreases, the frequency of each cycle increases due to decreasing spring softening of the microcantilever as it moves farther from the counter electrode as previously described herein above. This effect is shown in FIG. 20.

Figure 21A:
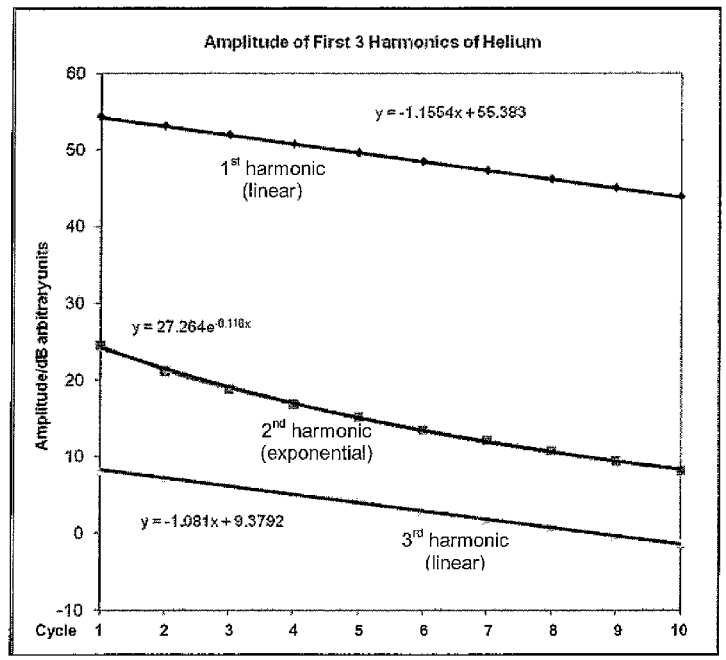
FIGS. 21A and 21B together are graphical representations of amplitude (FIG. 21A) and phase (FIG. 21B) of signals recorded as a function of cycle in an example construction of the second embodiment of the present subject matter where the element and counter electrode were operated in a helium (He) environment.
Figure 21B:
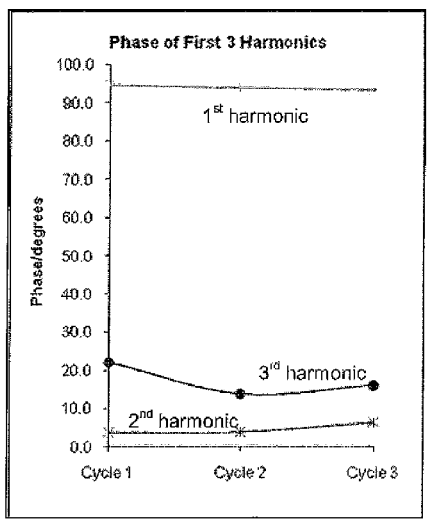

The harmonic amplitudes (Table 1 and FIG. 21A) can be graphed as functions of cycle with their own representative functions. The harmonic phases (Table 2 and FIG. 21B) can also be graphed as functions of cycle with their own representative functions. Along with the frequency shift in FIG. 20, these graphs represent all the independent numbers that comprise the mechanical output waveform from a nonlinearly vibrating cantilever such as described in accordance with an alternate embodiment of the present subject matter.

TABLE 1

Helium harmonic amplitudes as a function of cycle.

|  | 1st Harmonic (db) | 2nd Harmonic (db) | 3rd Harmonic (db) |
|---|---|---|---|
| Cycle 1 | 54.277 | 24.570 | 8.073 |
| Cycle 2 | 53.070 | 21.171 | 7.186 |
| Cycle 3 | 51.899 | 18.795 | 6.289 |
| Cycle 4 | 50.738 | 16.852 | 5.136 |
| Cycle 5 | 49.590 | 15.192 | 4.339 |
| Cycle 6 | 48.435 | 13.565 | 2.797 |
| Cycle 7 | 47.284 | 12.111 | 1.658 |
| Cycle 8 | 46.136 | 10.741 | 0.620 |
| Cycle 9 | 45.006 | 9.370 | −0.384 |
| Cycle 10 | 43.847 | 8.157 | −1.378 |

TABLE 2

Helium harmonic phases as a function of cycle.

|  | He 1st Harmonic (db) | He 2nd Harmonic (db) | He 3rd Harmonic (db) |
|---|---|---|---|
| Cycle 1 | 94.6 | 3.8 | 22.1 |
| Cycle 2 | 93.9 | 4.0 | 13.8 |
| Cycle 3 | 93.4 | 6.5 | 16.1 |

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. A method of determining characteristics within an environment, comprising:
   providing an at least semi-conductive element;
   locating a counter electrode a predetermined distance from the element such that the element and the counter electrode are in a non-contacting relationship;
   locating the at least semi-conductive element and the counter electrode within an environment;
   inducing an electrostatic force on the element by applying a first electrical signal, composed of an AC waveform and a DC component, between the counter electrode and the element, the AC waveform being applied in a pulsed ring-down mode having an on state and an off state, the element being allowed to freely oscillate in a non-linear field resulting from the DC component of the first electrical signal during the off state of the AC waveform;
   generating a second electrical signal in response to changes in distance between the counter electrode and element based on movement influenced by the induced electrostatic force and the environment; and
   examining the waveform of the second electrical signal during the off state of the AC waveform to analyze time dependent variations in frequency, amplitude, or phase of non-linear oscillations and their harmonics within the second electrical signal.

2. The method according to claim 1, wherein the element is a single-clamped or doubly clamped cantilever.

3. The method according to claim 1, wherein the element comprises a carbon-based nanostructure.

4. The method according to claim 1, wherein the second electrical signal is examined to ascertain characteristics of the element and its environment.

5. The method according to claim 1, further comprising:
   introducing one or more chemical species into the environment,
   wherein the second electrical signal is examined to ascertain characteristics of the one or more chemical species.

6. The method according to claim 1, wherein the method is carried out at ambient conditions.

7. The method according to claim 1, further comprising interacting a chemical species with the element, wherein said interaction changes a characteristic of the element.

8. The method according to claim 7, wherein the interaction is adsorption of the species on to the element.

9. The method according to claim 1, wherein examining the second electrical signal comprises examining the substantial entirety of the time domain waveform of the second electrical signal directly to analyze time dependant variations in frequency, amplitude, and phase of non-linear oscillations and their harmonics within the second electrical signal, or by comparing the time domain waveform with a computer simulation of the time domain waveform.

10. The method according to claim 1, wherein said second electrical signal is generated by the change in voltage produced by the oscillatory change in capacitance between the counter electrode and the element.

11. An electrical device comprising:
   an at least semi-conductive element;
   a counter electrode located a predetermined distance from the element such that the element and the counter electrode are in a non-contact mode;
   a signal generator for applying a first electrical signal between the element and the counter electrode to induce an electrostatic force on the element, the first electrical signal composed of an AC waveform and a DC component, the AC waveform being applied in a pulsed ring-down mode having an on state and an off state, the element being allowed to freely oscillate in a non-linear field resulting from the DC component of the first electrical signal during the off state of the AC waveform; and
   a signal processor for examining a second electrical signal generated based on changes in distance between the element and the counter electrode in response to the induced electrostatic force, and forces in the environment,
   wherein the signal processor is configured to examine the waveform of the second electrical signal during the off state of the AC waveform to analyze time dependent variations in frequency, amplitude, or phase of non-linear oscillations and their harmonics within the second electrical signal.

12. The electrical device of claim 11, wherein the element and the counter electrode are in a parallel arrangement.

13. The electrical device of claim 11, wherein the element and the counter electrode are in a tip-to-tip arrangement.

14. The electrical device of claim 11, wherein the element is a single-clamped cantilever.

15. The electrical device of claim 11, wherein the element is a double-clamped beam.

16. The electrical device of claim 11, wherein the element comprises a carbon-based nanostructure.

17. The electrical device of claim 11, further comprising a stage for location of a species, wherein interaction of the species with the element alters characteristics of the element.

18. The electrical device of claim 11, wherein the device is an atomic force microscope.

19. The electrical device of claim 11, wherein the signal processor is configured to examine the second electrical signal by examining the substantial entirety of the time domain waveform of the second electrical signal directly to analyze time dependant variations in frequency, amplitude, and phase of non-linear oscillations and their harmonics within the second electrical signal, or by comparing the time domain waveform with a computer simulation of the time domain waveform.

20. The electrical device of claim 11, wherein said second signal is generated by the change in voltage produced by the oscillatory change in capacitance between the counter electrode and the element.

\* \* \* \* \*

UNITED STATES PATENT AND TRADEMARK OFFICE
CERTIFICATE OF CORRECTION

PATENT NO. : 8,384,372 B1
APPLICATION NO. : 12/573433
DATED : February 26, 2013
INVENTOR(S) : Herbert W. Behlow, Jr. et al.

It is certified that error appears in the above-identified patent and that said Letters Patent is hereby corrected as shown below:

In the Specification

Column 1, lines 19-20 -- please correct "...National Science Foundation Grant No. 2003863" to read "...National Science Foundation Grant No. DMR-0304019."

Signed and Sealed this
Twenty-sixth Day of May, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,384,372 B1 | Page 1 of 1 |
| APPLICATION NO. | : 12/573433 | |
| DATED | : February 26, 2013 | |
| INVENTOR(S) | : Herbert W. Behlow, Jr. et al. | |

It is certified that error appears in the above-identified patent and that said Letters Patent is hereby corrected as shown below:

In the specification

Column 1, lines 18-20, please correct -- "The United States Government may have rights in this invention pursuant to National Science Foundation Grant No. 2003863." -- to read -- "This invention was made with government support under NSF grant #DMR-0304019. The government has certain rights in the invention, 37 CFR 401.14(f)(4)." --

Signed and Sealed this
Second Day of February, 2016

Michelle K. Lee
*Director of the United States Patent and Trademark Office*